US009964547B2

(12) United States Patent
Staffler et al.

(10) Patent No.: US 9,964,547 B2
(45) Date of Patent: May 8, 2018

(54) METHOD FOR DETECTING ASYN-SPECIFIC ANTIBODIES IN A BIOLOGICAL SAMPLE

(71) Applicant: AFFIRIS AG, Vienna (AT)

(72) Inventors: Guenther Staffler, Vienna (AT); Markus Mandler, Vienna (AT); Andreas Mairhofer, Vienna (AT); Arne Von Bonin, Vienna (AT)

(73) Assignee: AFFIRIS AG, Vienna (AT)

( * ) Notice: Subject to any disclaimer, the term of this patent is extended or adjusted under 35 U.S.C. 154(b) by 0 days. days.

(21) Appl. No.: 14/782,078

(22) PCT Filed: Apr. 2, 2014

(86) PCT No.: PCT/EP2014/056588
§ 371 (c)(1),
(2) Date: Oct. 2, 2015

(87) PCT Pub. No.: WO2014/161879
PCT Pub. Date: Oct. 9, 2014

(65) Prior Publication Data
US 2016/0054333 A1 Feb. 25, 2016

(30) Foreign Application Priority Data
Apr. 3, 2013 (EP) ..................................... 13162107

(51) Int. Cl.
*G01N 33/68* (2006.01)
*G01N 33/564* (2006.01)
(52) U.S. Cl.
CPC ....... *G01N 33/6854* (2013.01); *G01N 33/564* (2013.01); *G01N 33/6896* (2013.01); *G01N 2800/2814* (2013.01)

(58) Field of Classification Search
None
See application file for complete search history.

(56) References Cited

U.S. PATENT DOCUMENTS

| 6,524,793 | B1 | 2/2003 | Chandler et al. |
| 2005/0118574 | A1 | 6/2005 | Chandler et al. |
| 2011/0300077 | A1 | 12/2011 | Weihofen et al. |
| 2013/0052200 | A1 | 2/2013 | Dodel et al. |

FOREIGN PATENT DOCUMENTS

| CN | 102317316 A | 1/2012 |
| EP | 2 366 714 A1 | 9/2011 |
| WO | WO 97/14028 A2 | 4/1997 |
| WO | WO 2010/069603 A1 | 6/2010 |

OTHER PUBLICATIONS

El-Agnaf et al., FEBS Letters, 440:71-75 (1998).*
Minguez-Castellanos et al., Neurology, 68:2012-2018 (2007).*
Masliah et al., PLoS ONE, 6(4):e19338, Apr. 2011.*
Baba et al., Am J Pathol., 152(4):879-884, Apr. 1998.*
Emadi et al., J Biol Chem, 284(17):11048-11058, Apr. 2009.*
Iwatsubo et al., Am J Pathol, 148(5):1517-1529, May 1996.*
Papachroni et al., J Neurochem., 101:749-756, 749-756, 2007.*
Combined Chinese Office Action and Search Report dated Aug. 1, 2016 in Patent Application No. 201480029965.1 (submitting English translation only).
Zhang Chen, et al., "Preparation and Identification of the aggregates of mutant alpha-synucleins linked to familial Parkinson disease" Chinese Journal of Clinical Rehabilitation, vol. 9, No. 13, Apr. 7, 2005, pp. 39-41 and p. 13-1 (with English Abstract).
David J. Brooks, "Imaging Approaches to Parkinson Disease" The Journal of Nuclear Medicine, vol. 51, No. 4, Apr. 2010, pp. 596-609.
Jeffrey L. Cummings, et al., "The role of dopaminergic imaging in patients with symptoms of dopaminergic system neurodegeneration" Brain, vol. 134, 2011, pp. 3146-3166.
Bruno Dubois, et al., "Revising the definition of Alzheimer's disease: a new lexicon" Lancet Neurol., vol. 9, Nov. 2010, pp. 1118-1127.
Thibaud Lebouvier, et al., "Colonic Biopsies to Assess the Neuropathology of Parkinson's Disease and Its Relationship with Symptoms" PLoS ONE, e12728, vol. 5, No. 9, Sep. 2010, 9 Pages.
Kathleen M. Shannon, et al., "Alpha-Synuclein in Colonic Submucosa in Early Untreated Parkinson's Disease" Movement Disorders, vol. 27, No. 6, 2012, pp. 709-715.
Roberta Borghi, et al., "Full length α-synuclein is present in cerebrospinal fluid from Parkinson's disease and normal subjects" Neuroscience Letters, vol. 287, 2000, pp. 65-67.
P. H. Lee, et al., "The plasma alpha-synuclein levels in patients with Parkinson's disease and multiple system atrophy" Journal of Neural Transmission, vol. 113, 2006, pp. 1435-1439.
Qiao-Xin Li, et al., "Plasma α-synuclein is decreased in subjects with Parkinson's disease" Experimental Neurology, vol. 204, 2007, pp. 583-588.
Omar M. A. El-Agnaf, et al., "Detection of oligomeric forms of α-synuclein protein in human plasma as a potential biomarker for Parkinson's disease" The FASEB Journal, vol. 20, Mar. 2006, pp. 419-425.
Lynnae M. Smith, et al., "α-Synuclein and Anti-α-Synuclein Antibodies in Parkinson's Disease, Atypical Parkinson Syndromes, REM Sleep Behavior Disorder, and Healthy Controls" PLoS ONE, e52285, vol. 7, No. 12, Dec. 2012, 9 Pages.
Yu Wang, et al., "Phosphorylated α-Synuclein in Parkinson's Disease" Sci. Transl. Med, vol. 4, No. 121, Feb. 15, 2012, 15 Pages.

(Continued)

*Primary Examiner* — Kimberly Ballard
*Assistant Examiner* — Stacey MacFarlane
(74) *Attorney, Agent, or Firm* — Oblon, McClelland, Maier & Neustadt, L.L.P.

(57) ABSTRACT

Disclosed is a method for detecting aSyn-specific antibodies in a biological sample, comprising the following steps: —contacting the sample with aSyn-comprising-aggregates and allowing the aSyn-specific antibodies to bind to the aSyn-comprising-aggregates, and —detecting the aSyn-specific antibodies bound to the aSyn-comprising-aggregates by a single particle detection technique, preferably by fluorescence activated cell sorting (FACS).

19 Claims, 10 Drawing Sheets

(56) References Cited

OTHER PUBLICATIONS

Figure 1:
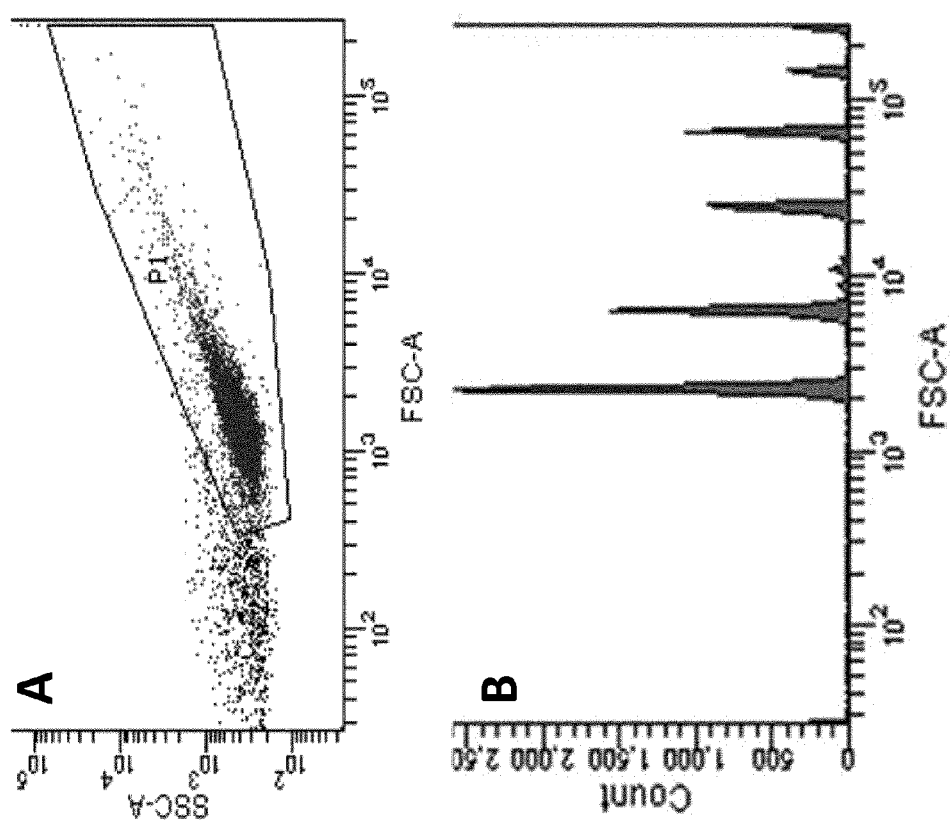

J.M. Woulfe, et al., "Absence of elevated anti-a-synuclein and anti-EBV latent membrane protein antibodies in PD" Neurology, vol. 58, 2002, pp. 1435-1436.

L M. Patrias, et al., "Specific antibodies to soluble alpha-synuclein conformations in intravenous immunoglobulin preparations" Clinical and Experimental Immunology, vol. 161, 2010, pp. 527-535.

Marina A. Gruden, et al., "Immunoprotection against toxic biomarkers is retained during Parkinson's disease progression" Journal of Neuroimmunology, vol. 233, 2011, pp. 221-227.

Kiran Yanamandra, et al., "α-Synuclein Reactive Antibodies as Diagnostic Biomarkers in Blood Sera of Parkinson's Disease Patients" PLoS ONE, e18513, vol. 6, No. 4, Apr. 2011, 13 Pages.

Marina A. Gruden, et al., "Correlation between Protective Immunity to α-Synuclein Aggregates, Oxidative Stress and Inflammation" Neuroimmunomodulation, vol. 19, 2012, pp. 334-342.

Daniela Besong-Agbo, et al., "Naturally occurring α-synuclein autoantibody levels are lower in patients with Parkinson disease" Neurology, vol. 80, Jan. 8, 2013, pp. 169-175.

Harald Hampel, et al., "Biomarkers for Alzheimer's disease: academic, industry and regulatory perspectives" Nature Reviews Drug Discovery, vol. 9, Jul. 2010, pp. 560-574.

Neelam Shahani, et al., "Tau Aggregation and Progressive Neuronal Degeneration in the Absence of Changes in Spine Density and Morphology after Targeted Expression of Alzheimer's Disease-Relevant Tau Constructs in Organotypic Hippocampal Slices" The Journal of Neuroscience, vol. 26, No. 22, May 31, 2006, pp. 6103-6114.

Diane P. Hanger, et al., "Tau phosphorylation: the therapeutic challenge for neurodegenerative disease" Trends in Molecular Medicine, vol. 15, No. 3, 2009, pp. 112-119.

SR Binder, "Autoantibody detection using multiplex technologies" Lupus, vol. 15, 2006, pp. 412-421.

Matthew R. Janes, et al., "Next-generation flow cytometry" Nature Biotechnology, vol. 29, No. 7, Jul. 2011, pp. 602-604.

Dr. Ronacher, "Reverse Array for OnSpot Immunogenicity Measurement" Anagnostics Technical Note, ANA-TN-005, Feb. 2010, 2 Pages.

Michelle J. Cannon, et al., "Kinetic analysis of beta-amyloid fibril elongation" Analytical Biochemistry, vol. 328, 2004, pp. 67-75.

Sotiris Missailidis, et al., "Characterization of Antibody-Antigen Interactions by Fluorescence Spectroscopy" Methods in Molecular Biology, vol. 248, 2004, pp. 431-441.

Valerie L. Anderson, et al., "Transmission electron microscopy characterization of fluorescently labelled amyloid β 1-40 and α-synuclein aggregates" BMC Biotechnology, vol. 11, No. 125, 2011, 10 pages.

Extended European Search Report dated Jul. 23, 2013 in Patent Application No. 13162107.0.

International Search Report dated Jun. 24, 2014 in PCT/EP2014/056588.

Written Opinion dated Jun. 24, 2014 in PCT/EP2014/056588.

Kim Spells, et al., "Specificity of HLA antibodies detected with HLA antigen-coated polystyrene beads." 29th Annual Meeting of the American Society for Histocompatibility and Immunogenetics, XP055070270, 2003, 1 Page.

Katerina K. Papachroni, et al., "Autoantibodies to alpha-synuclein in inherited Parkinson's disease" Journal of Neurochemistry, vol. 101, XP002530228, 2007, pp. 749-756.

Mihaela M. Apetri, et al., "Secondary Structure of α-Synuclein Oligomers: Characterization by Raman and Atomic Force Microscopy" Journal of Molecular Biology, vol. 355, XP005197985, 2006, pp. 63-71.

Qingyou Li, et al., "Improvement of a low pH antigen-antibody dissociation procedure for ELISA measurement of circulating anti-Aβ antibodies" BMC Neuroscience, vol. 8, No. 22, XP021022581, Mar. 20, 2007, 11 Pages.

J. Jankovic, "Parkinson's disease: clinical features and diagnosis" J. Neurol. Neurosurg. Psychiatry, vol. 79, 2008, pp. 368-376.

DJ Gelb, et al., "Criteria for the diagnosis of Parkinson's disease" Arch. Neurol., vol. 56, No. 1, 1999, 1 Page.

S. Gilman, et al., "Second consensus statement on the diagnosis of multiple system atrophy" Neurology, vol. 71, Aug. 26, 2008, pp. 670-676.

Combined Office Action and Search Report dated Mar. 20, 2017 in Chinese Patent Application No. 201480029965.1 (submitting English language translation only).

Kevin C. O'Connor, et al., "Self-antigen tetramers discriminate between myelin autoantibodies to native or denatured protein", Nature Medicine, Technical Reports, vol. 13, No. 2, Feb. 2007, pp. 211-217.

Office Action as received in the corresponding Japanese Application No. 2016-505803 dated Jan. 9, 2018 citing documents AX and AY, 8 pages.

Gruden, M.A. et al.,"Immunoprotection against toxic biomarkers is retained during Parkinson's disease progression," Journal of Neuroimmunology, 2011, vol. 233, pp. 221-227.

Patrias, L.M. et al., "Specific antibodies to soluble alpha-synuclein conformations in intravenous immunoglobulin preparation", Clinical and Experimental Immunology, 2010, vol. 161, pp. 527-535.

* cited by examiner

METHOD FOR DETECTING ASYN-SPECIFIC ANTIBODIES IN A BIOLOGICAL SAMPLE

The present invention relates to methods for detecting alpha Synuclein (aSyn)-specific antibodies in biological samples, especially in connection with and for diagnosing of Synucleinopathies, including Parkinson's disease (PD), Lewy Body Disease (LBD), Dementia with Lewy Bodies (DLB), Parkinson's Disease Dementia (PDD), Multiple System Atrophy (MSA), Pure Autonomic Failure (PAF), REM Sleep Behavior Disorder (RBD), Neurodegeneration with Brain Iron Accumulation type I (NBIA Type I) and inclusion body myositis (IBM). The present invention further relates to methods for detecting alpha Synuclein (aSyn)-specific antibodies in biological samples, especially in connection with and for diagnosing of diseases with alpha synuclein deposition and/or aggregation, including Alzheimer's disease (AD), Down Syndrome (DS), Progressive Supranuclear Palsy (PSP), Corticobasal Degeneration (CBD), Frontotemporal Dementia/Pick's Disease (FTD/PiD).

Synucleinopathies are a diverse group of neurodegenerative disorders that share a common pathologic characteristic: in neuropathologic examinations characteristic lesions can be detected containing abnormal aggregates of aSynuclein (aSyn) protein in selected populations of neurons and glia cells.

aSyn (initially identified as PARK1 and PARK4) is a 140 amino acid protein widely expressed in the neocortex, hippocampus, dentate gyrus, olfactory bulb, striatum, thalamus and cerebellum as well as in peripheral neurons and ganglia, e.g.: in colon or muscle tissue. The major form of the protein is the full 140 amino acids-long transcript. Other isoforms are alpha-synuclein-98, lacking exon 3 and 5, alpha-synuclein-126, where exon 3 is lost and lacks residues 41-54; and alpha-synuclein-112, which lacks residue 103-130 due to loss of exon 5. aSyn is also highly expressed in hematopoietic cells including B-, T-, and NK cells as well as monocytes and platelets. The exact role in these cells is not known but it has been implicated in the differentiation of megakaryocytes (platelet precursors).

The most common synucleinopathies include Parkinson's disease (PD), Lewy Body Disease (LBD), Dementia with Lewy Bodies (DLB), Parkinson's Disease Dementia (PDD), Multiple System Atrophy (MSA), Pure Autonomic Failure (PAF), REM Sleep Behavior Disorder (RBD), Neurodegeneration with Brain Iron Accumulation type I (NBIA Type I) and Inclusion Body Myositis (IBM).

The current treatment options for these diseases include symptomatic medications such as L-dopa, Dopamine agonists, anticholinergic drugs as well as inhibitors of monoamine oxidase. However, all treatment opportunities currently present only lead to symptomatic alleviation but do not induce a long lasting, disease modifying effect in patients.

Lewy body disorders (LBD) are progressive neurodegenerative disorders characterized by tremor, rigidity, bradykinesia and by loss of dopaminergic neurons in the brain. In the case of DLB and PDD signs also include cognitive impairment. Up to 2% of the population above 60 years of age in western countries develop the typical signs of PD/LBD. Currently only symptomatic treatment is available. Unfortunately, these therapies only provide temporary relief from early symptoms and do not halt disease progression. The pathogenesis of PD/LBD is still incompletely understood, but it appears that genetic susceptibility and environmental factors are involved in the development of the disease. Despite all genetic advances, PD/LBD is primarily a sporadic disorder with no known cause (also called idiopathic PD/LBD).

Patients suffering from this disease develop characteristic ubiquitinated intracellular inclusions called Lewy bodies (LBs) in the cortical and subcortical areas of the brain as well as in peripheral neurons or ganglia, e.g.: in colonic ganglia. Especially regions with high content of dopaminergic neurons or neuronal projections show this typical pathologic feature. Recently, several studies could show that the synaptic protein aSyn plays a central role in LBD pathogenesis. In LBD, aSyn accumulates in LBs throughout affected brain areas or peripheral neurons and ganglia. Additionally, it could be demonstrated that single point mutations as well as gene dosage alterations of aSyn (e.g.: duplications or multiplications in the aSyn gene) are associated with rare familial forms of parkinsonism. Importantly, based on results from overexpression studies in transgenic (tg) mice as well as in *Drosophila melanogaster* its key role in the pathogenesis of PD/LBD is underscored as these animal models mimic several characteristics of PD/LBD/DLB.

Another very important synucleinopathy is Multiple System Atrophy (MSA). MSA is a sporadic neurodegenerative disorder that is characterised by symptoms of L-DOPA-resistant parkinsonism, cerebellar ataxia, and dysautonomia. Patients suffer from multisystem neuronal loss affecting various brain areas including striatum, substantia nigra, cerebellum, pons, as well as the inferior olives and the spinal cord. MSA is characterized by aSyn-positive glial cytoplasmic (GCI) and rare neuronal inclusions throughout the central nervous system. These inclusions are associated with striato-nigral degeneration, olivo-ponto-cerebellar atrophy, and involvement of autonomic nuclei in medulla and spinal cord. The importance of GCIs for the pathogenesis of MSA is generally acknowledged and underscored by recent analysis of transgenic mouse models analysing the effect of aSyn overexpression in oligodendroglia. In tg mice overexpressing human aSyn both, GCI-like aggregates and biochemical markers of MSA were observed.

Although the exact mechanisms by which accumulation of aSyn leads to the typical features of neurodegeneration in synucleopathies are not fully understood, recent studies imply that abnormal formation and accumulation of aSyn is involved in the degenerative processes underlying synucleinopathies. Recently, different forms of aSyn have been identified in LBs. Beside the full length form of the protein, different forms of modified aSyn have been identified including phosphorylated, nitrosylated/nitrated, acetylated and mono-, di-, or tri-ubiquitinated aSyn. In addition, C-terminally truncated forms of the protein, like aSyn 1-119, aSyn 1-122 and aSyn 1-123, have been detected in brain tissue from both transgenic mice and PD/MSA cases.

It is currently believed that up to 15% of the aSyn detected in LBs and lewy neurites or GCIs is truncated. Previous in vitro studies using truncated aSyn could demonstrate that aSyn lacking the C-terminal 20-30 amino acids was showing an increased tendency to aggregate and to form filaments found in Lewy-neurites and LBs. In addition, approximately 90% of aSyn deposited in LBs is phosphorylated at serine 129 (Ser129). In contrast, only 4% of total aSyn is phosphorylated in normal brain, suggesting that accumulation of Ser129-phosphorylated aSyn might be crucial in the pathogenesis of PD. Therefore, these truncated and/or modified forms of aSyn are thought to act as seed molecules for formation of aSyn oligomers/fibrils. Thus full length aSyn as well as truncated and/or modified forms of aSyn are then believed to accumulate leading to aggregate-formation. Based on recent studies it is believed that such aggregate-formation, (i.e. oligomers and fibrils) for example in the synaptic terminals and axons, plays an important role for PD/LBD/synucleinopathy development and could thus be enhanced by the presence of truncated/modified forms of aSyn.

The diagnosis of synucleinopathies, especially LBD/PD and MSA, is a purely clinical one based on the gradual occurrence of bradykinesia and at least one of the following aberrations: muscular rigidity, 4-6 Hz resting tremor and/or postural instability not caused by primary visual, vestibular, cerebellar or proprioceptive dysfunction (Jankovic J. et al. J. Neurol. Neurosurg. Psychiatr. (2008) 79 (4): 368-76. criteria: United Kingdom Parkinson's Disease Society Brain Bank Diagnostic Criteria for Parkinson's Disease and Criteria of diagnosis of Parkinson disease (Gelb et al., 1999) commissioned and supported by the Advisory Council of the National Institute of Neurological Disorders and Stroke, U.S. National Institutes of Health). In addition diagnosis of PD/LBD critically depends on the fulfillment of additional supporting clinical signs and the exclusion of other causes that can secondarily produce a parkinsonian syndrome like Alzheimer's disease, multiple cerebral infarction and drug-induced parkinsonism. Parkinson plus syndromes such as progressive supranuclear palsy and multiple system atrophy must be ruled out as well to establish a probable PD/LBD diagnosis.

For MSA, diagnosis of probable MSA requires a sporadic, progressive adult-onset disorder including rigorously defined autonomic failure and poorly levodopa-responsive parkinsonism or cerebellar ataxia (Gilman et al. Neurology. (2008) Aug. 26; 71(9):670-6. Second consensus statement on the diagnosis of multiple system atrophy.).

The limitation of clinical diagnosis of PD/LBD/MSA are high rates of misdiagnoses (diagnostic specificity evaluated at autopsy is 75-90%, with specialists such as neurologists having the highest rates; Jankovic J J. Neurol. Neurosurg. Psychiatr. (2008) 79 (4): 368-76.) and the fact that the diagnosis could only be made at a late time point when the disease had caused substantial neuronal loss that resulted in functional deficits.

In addition to clinical diagnosis, state of the art imaging techniques are currently employed to substantiate diagnosis of synucleinopathies. Computed tomography and magnetic resonance imaging (MRI) brain scans of patients usually appear normal but analyses are used to exclude other secondary causes of parkinsonism, such as basal ganglia tumors, vascular pathology and hydrocephalus (Brooks D J et al. J. Nucl. Med. (2010) 51 (4): 596-609). However, specialized MRI techniques (e.g.: diffusion tensor imaging (DTI)) have demonstrated more consistent and promising results by exploring modifications of basal ganglia and mesencephalic structures. Dopaminergic imaging is further employed to differentiate forms of dopaminergic neurodegeneration (e.g.: PD/LBD) from other diseases not affecting the dopaminergic system. This imaging can be performed using either single-photon emission computed tomography (SPECT) or PET. For example in patients with diagnostic uncertainty between degenerative parkinsonism and non-degenerative tremor disorders, baseline imaging with the dopamine transporter ligand [123I]ioflupane (DaTscan™) has shown 78% sensitivity and 97% specificity with reference to clinical diagnosis at 3 years, versus 93% and 46%, respectively, for baseline clinical diagnosis (Cummings J L et al., Brain. (2011); 134(11):3146-3166.)

The current algorithms for diagnosing synucleinopathies suffer from the lack of sensitivity and specificity for a secure diagnosis at early stages of disease. In order to enhance the diagnostic capacities, clinical as well as imaging data have to be used in combination with patho-physiologically meaningful changes in disease-specific biomarkers. Such changes as exemplified in Alzheimer's disease with hippocampal atrophy as assessed by structural MRI; AD-typical cerebrospinal fluid signature (low Aβ42, high total tau, high phospho-Tau); positive amyloid imaging; defined genetic risk; have been a basis for a fundamental change in the diagnostic procedures (Dubois et al., Lancet Neurol. 9 (2010): 1118-1127) for AD as advised by international regulatory bodies and interest groups including the National Institute of Aging (NIA, NIH, USA), the NIH NINCDS working group, and the Alzheimer Association.

Unfortunately, no such validated biomarker data are available until now for PD/LBD/MSA. However, an international consortium of clinical and biomedical researchers under the lead of the Michael J Fox Foundation for Parkinson's disease has initiated the Parkinson's disease progressive Markers Initiative (PPMI) recently, a landmark observational clinical study to comprehensively evaluate a cohort of recently diagnosed PD patients and healthy subjects using advanced imaging, biologic sampling and clinical and behavioural assessments to identify biomarkers of Parkinson's disease progression. One of the main objectives is to evaluate changes in aSyn levels in different body fluids as potential biomarker for disease progression in synucleinopathies. This objective is based on the potential central role of aSyn for disease progression as well as on the identification of aSyn in different body tissues and fluids. Studies by Lebouvier et al. and Shannon et al. demonstrated aSyn pathology in peripheral tissue of PD patients (Lebouvier et al., PLoS ONE (2010) 5(9): e12728; Shannon et al., Mov. Disord. (2012) 27: 709-715). aSyn has also been identified in the CSF and plasma of synucleinopathy patients and healthy controls (Borghi et al. Neuroscience Letters, (2000) 287: 1, pp 65-67; Journal of Neural Transmission (2006), 113, 10, pp 1435-1439; Lee et al., Experimental Neurology, (2007) 204: 2, pp 583-588). Interestingly, there is conflicting evidence on the level of aSyn in healthy and diseased subjects as a recent study by Qiao-Xin Li et al. (Experimental Neurology, (2007) 204: 2, pp 583-588) indicated that aSyn levels in plasma from PD subjects are significantly lower than that in age-matched controls ($p=0.001$), and the aSyn levels in patients with early-onset PD are lower than that in both late-onset PD and controls, whereas Lee et al. showed that plasma aSyn levels are indeed increased in PD and MSA patients as compared to controls. El-Agnaf and colleagues could demonstrate the presence of aggregated (oligomerised) aSyn in human plasma and report the presence of significantly elevated ($P=0.002$) levels of oligomeric forms of aSyn in plasma samples obtained from 34 PD patients compared with 27 controls; (El-Agnaf et al., FASEB J. (2006) 20, 419-425). Smith and colleagues (PLoS ONE (2012) 7(12): e52285 and references therein) showed that no significant differences of PD and non-PD patients could be detected. These discrepancies demonstrate the problems arising in validating novel biomarkers and underpin the necessity to identify novel and validated biomarkers for early diagnosis. In addition Wang et al. also demonstrated that CSF levels of post-translationally modified aSyn (pS129) correlated weakly with PD disease severity and, when combined with total aSyn concentrations, contributed to distinguishing PD from the second most prominent synucleinopathy, MSA and from a third neurodegenerative disease with proteopathic lesions containing among others synuclein, progressive supranuclear palsy (PSP). (Wang et al., Sci Transl Med. (2012) Feb. 15; 4(121))

In addition to the mere detection of various forms of aSyn in different tissues (i.e.: full length, truncated, phosphorylated (mainly at S129), nitrosylated and ubiquitinated aSyn; and oligomers and aggregates of these forms), several research groups were able to identify auto-antibodies directed against aSyn in serum/plasma or plasma products (e.g.: IVIG) from healthy and diseased patients suffering from idiopathic or inherited synucleinopathies. Woulfe et al. could detect anti aSyn Abs in PD patients already in 2002 (Neurology 58: (2002) 1435-1436.). Papachroni et al. examined the presence of Abs against synuclein family members in the peripheral blood serum of PD patients and control individuals by Western Blot analysis. Presence of Abs against monomeric β- or γ-synuclein did not show PD association. Multi-epitopic Ab against monomeric aSyn however, were detectable in 65% of all patients tested, strongly correlating with an inherited mode of the disease. The frequency of the Ab presence in patients with an idiopathic form of PD was not significantly different from the frequency in the control group but a very high proportion (90%) of patients with familial forms of PD were positive for Abs against aSyn (Papachroni et al., Journal of Neurochemistry, (2007) 101: 749-756.). Accordingly, Patrias et al. were also able to identify Abs specific to aSyn monomer and soluble oligomers (containing monomers as well as undefined aggregates of aSyn) in three intravenous immunoglobulin (IVIG) preparations obtained from healthy controls, Gamunex (Talecris Biotherapeutics), Gammagard (Baxter Healthcare) and Flebogamma (Grifols Biologicals). Antibodies were measured in native IVIG preparations and after antibody-antigen complex dissociation and reactivity was assessed by ELISA and Western blot.

Again different reports regarding the levels of anti aSyn Abs in healthy controls and diseased patients have been published, mainly based on the analysis by conventional ELISA and immunoblot techniques. In 2002, Woulfe et al. were not able to detect changes between PD and controls by ELISA. In contrast Gruden et al. (2011, 2012) and Yanamandra et al (2011) demonstrated that anti aSyn Abs are increased in PD patients as compared to controls, especially in early stages of the disease (highest increase in early PD (Hoehn and Yahr stage 1-2) and late PD (Hoehn and Yahr stage 2.5-4) as compared to controls. At later stages less increase was detectable in PD patients as compared to controls. Yamandra et al. could demonstrate by ELISA and Immuno Blot analysis of anti monomeric aSyn reactivity that 63% of individuals exhibiting the high responses in a group of early PD patients (5× in mean–10× increase in median levels as compared to controls). In the late PD group the immune responses declined, showing ca. 4 and 6 fold increase in mean and median, respectively (P,0.007), compared to controls and with ca. 58% of patients showing high level of antibodies. The diagnostic potentials of the ELISA and Western blot analysis in this report were also assessed statistically (receiver operating characteristic (ROC) analysis). The areas under the ROC curves (AUC) for the autoimmune reactivity determined by ELISA in early and late PD patients compared to controls were 0.884 (95% confidence interval of 0.79 to 0.97) and 0.779 (0.6-0.95), respectively. The AUC values calculated from the corresponding ROC curves for the Western blot data were 0.85 (0.74-0.95) for early PD vs controls and 0.817 (0.67-0.95) for late PD vs controls, respectively. This indicates that the autoimmune responses to monomeric aSyn have a diagnostic value both in early and late PD patients however with optimal settings allowing the identification of ca. 60% of patients only. No significant binding to oligomeric species of aSyn was detectable and analysis of reactivity to fibrillar aSyn also showed that no significant differences of early PD, late PD or controls were observed. The ROC analysis of the immune responses to fibrils in early/late PD patients vs controls gave the AUC values not greater than 0.5 and ROC curves close to diagonals indicating no or very limited diagnostic value. There were no significant correlations between the immune responses towards aSyn fibrils in PD patients and controls with their age or gender (Gruden et al., J Neuroimmunol 233 (2011): 221-227; Yanamandra et al., PLoS One 6 (2011): e18513; Gruden et al., Neuroimmunomodulation 19 (2012): 334-342).

In contrast, Besong-Agbo et al. showed that Ab levels are lower in PD patients as compared to healthy controls and patients suffering from Alzheimer's disease, whereas Smith and colleagues showed that there was no significant change comparing synucleinopathy patients and healthy controls (Neurology. 2013 Jan. 8; 80(2):169-75. Naturally occurring α-synuclein autoantibody levels are lower in patients with Parkinson disease (Besong-Agbo et al., PLoS ONE 7(12) (2012): e52285 and references therein).

WO 2010/069603 A1 and EP 2 366 714 A1 disclose a method for detecting aSyn specific antibodies in serum or plasma of patients with PD comprising detecting the antibodies with particles coated with aSyn. Papachroni et al. (J. Neurochem. 101 (2007): 749-756) report about autoantibodies to aSyn in inherited PD. Apetri et al. (J. Mol. Biol. 255 (2006): 63-71) analyse the secondary structure of aSyn oligomers by Raman and atomic force microscopy. There is no disclosure of the detection of aSyn aggregates being used for capture of anti-aSyn antibodies in blood.

WO 97/14028 A2 discloses multiplex analysis systems using "beadsets" labelled with specific markers and using FACS. Spells et al. (Abstract of the 29th annual meeting of the American Society for Histocompatibility and Immunogenetics: S113) report about the specificity of HLA antibodies detected with HLA antigen-coated polystyrene beads. Li et al. (BMC Neuroscience 8 (2007): 22) show the improvement of a low pH antigen-antibody dissociation procedure for ELISA measurement of circulating anti-Abeta antibodies.

In summary, so far, none of these methods (detection of aSyn, including full length, truncated or modified as well as aggregated forms or detection of antibodies specifically detecting them by Biacore, ELISA or Western Blot) fulfilled the criteria that would qualify them as predictive biomarker (>80% specificity) for PD/LBD/MSA or any other synucleinopathy.

Thus, there is still a lack of a reliable biomarker that can be applied repetitively, at low risk and costs. This is especially true since all efforts taken so far to develop blood-based AD, PD and MSA biomarkers failed (Hampel et al., Nat. Rev. Drug Discov. 9 (2010): 560-574). The availability of such a biomarker would be of outmost importance for the development of disease-modifying therapies. The earlier such therapies would be administered, the bigger the chances for success. And, one could limit such efforts to true PD and MSA cases identified with the help of a specific biomarker.

It is an object of the present invention to provide means for improving the diagnosis of synucleinopathies, including PD/LBD, DLB, PDD, PAF, RBD, MSA, NBIA type1, especially for tracking early stages of the disease and for observing the development of clinical trials for drugs for the treatment of synucleinopathies. It is a further object to provide reliable tools for detecting anti-aSyn antibodies in biological samples, especially in samples of human synucleinopathy patients or human individuals who are suspected to have or are at risk of developing a synucleinopathy, including PD/LBD, DLB, PDD, PAF, RBD, MSA, NBIA type1, IBM.

Therefore, the present invention provides a method for detecting aSyn-specific antibodies in a biological sample comprising the following steps:
  contacting the sample with aSyn-comprising-aggregates, especially aSyn-consisting-aggregates, and allowing the aSyn-specific antibodies to bind to the aSyn-comprising-aggregates, and
  detecting the aSyn-specific antibodies bound to the aSyn-comprising-aggregates by a single particle detection technique, preferably by fluorescence activated cell sorting (FACS).

With the present invention, a new method to detect aSyn-specific antibodies, especially aSyn-specific auto-antibodies is disclosed which can be used as diagnostic tool which is extremely helpful in diagnosing of synucleinopathies, including PD/LBD, DLB, PDD, PAF, RBD, MSA, NBIA type1, and monitoring the development of these diseases, as well as for diseases like Alzheimer's disease (AD), Down Syndrome (DS), PSP, CBD, FTD/PiD. The present method is based on the invention that not just single aSyn peptides are used as capturing tools for the aSyn-specific antibodies, but that instead aggregates consisting of aSyn ("aSyn-consisting-aggregates") or comprising i.a. aSyn ("aSyn-comprising-aggregates") are used and that thereby generated antibody-aSyn-aggregate complexes are detected using a single particle detection technique. If both, aSyn-comprising-aggregates and aSyn-consisting-aggregates are referred to herein, also the term "aSyn-aggregates" is used which is meant as "aSyn-comprising-aggregates, especially aSyn-consisting-aggregates", because the latter are a preferred embodiment of the aSyn-aggregates according to the present invention.

Briefly, aSyn-consisting-aggregates are aggregates consisting of full-length aSyn protein (the 140 aa long protein as disclosed above). aSyn-consisting-aggregates are aggregates consisting of full-length aSyn protein (the 140 aa long protein as disclosed above). aSyn-comprising-aggregates contain aSyn protein besides other components, especially other amyloidogenic polypeptides, such as Aβ1-42, Aβp(E)3-42 (or other Aβ forms), islet amyloid polypeptide, Tau protein (including phosphorylated Tau), TAR-DNA binding protein 43 (TDP43). For the purpose of the present invention, the term "aSyn-comprising-aggregates" also encompasses aggregates that contain—instead or besides aSyn (the full length aSyn 140 aa protein)—aSyn polypeptides that are truncated or modified, especially aSyn polypeptides that are naturally occurring forms of aSyn, such as aSyn-98 (lacking exon 3 and 5), aSyn-126 (lacking aa 41-54; loss of exon 4) and aSyn-112 (lacking aa 103-130; loss of exon 5), phosphorylated (especially at serin 129—Ser129), nitrosylated/nitrated, acetylated and mono-, di-, or tri-ubiquitinated aSyn, or C-terminally truncated forms of aSyn such as aSyn lacking the C-terminal 20, preferably lacking the C-terminal 25, especially lacking the C-terminal 30 amino acids. The prerequisite for such aggregate components, especially the aSyn variants disclosed above, is that these components are capable of forming aggregates (i.e. capable of forming aggregates under conditions applied according to the disclosure according to the present invention, especially in the example section).

The aSyn-aggregates according to the present invention are generated e.g. by overnight incubation of the aggregate-forming proteins, e.g. aSyn or aSyn and other aggregate proteins/polypeptides, such as Aβ polypeptides (especially Aβ1-42, Aβp(E)3-42 (or other Aβ forms)), islet amyloid polypeptide, tau protein, TDP43; and/or aSyn polypeptides that are truncated or modified. Subsequently, aSyn-(containing or comprising)-aggregates are incubated with serum samples derived either from healthy donors (HD) or from patients, especially PD and MSA patients or patients suspected of having PD and MSA, to allow binding of present antibodies (both IgG and IgM). Antibodies bound to the aSyn-comprising-aggregates, especially the aSyn-consisting-aggregates can be detected by any suitable method available to a person skilled in the art, e.g. by using a labelled secondary antibody which recognises the aSyn-specific antibody bound to the aSyn-aggregates. For example a phycoerythrin (PE)-labelled secondary antibody can be used. Thereafter, the immune complexes comprising the aSyn-specific antibody bound to the aSyn-aggregates (and optionally one or more detection agents, such as secondary antibodies) are measured using a single particle detection technique, such as FACS (fluorescence activated cell sorting)-analysis also known as flow cytometry. The level of aSyn-specific antibodies obtained for a given sample can then be compared to the level of a healthy sample or to the level in a sample of a patient with a known disease status, for example the level in a sample of a PD and MSA patient. Using the method according to the present invention, it could be shown that PD and MSA patients contain different levels of aSyn-specific immunoglobulins which are reactive towards the aSyn-aggregates (free aSyn-specific immunoglobulins) provided according to the present invention compared to healthy subjects. Furthermore, using the method according to the present invention, it could be shown that reactivity of aSyn-specific immunoglobulins (towards the aSyn-aggregates provided according to the present invention) derived from PD and MSA patients can be increased by a procedure known as demasking (removing of potentially bound aSyn-antigens from autoantibodies). This is in contrast to the reactivity of aSyn-specific immunoglobulins from healthy subjects where such an increase of reactivity towards the aSyn-aggregates cannot be detected after treating these sera in a special way. On the other hand, the reactivity of IgM-antibodies after demasking (=dissociation of already bound aSyn in the serum) revealed an increased level of IgM in PD and MSA patients. Additionally, also the difference between IgG levels with and without demasking was determined (delta (Δ) values). This parameter was also elevated in PD and MSA patients as compared to healthy controls showing higher antibody occupancy by aSyn of antibodies in the pathological state of the disease. Furthermore, with the present invention data are provided showing that the present method has a much higher capacity to detect aSyn-specific antibodies and thus has a much higher power to diagnose e.g. PD and MSA compared to methods published so far. Given these facts, the method according to the present invention fulfils the theoretical prerequisites of a predictive diagnostic tool to identify synucleinopathies, especially PD and MSA, and to follow the clinical response of a given patient to treatment.

The present invention was developed for the analysis of aSyn-specific antibodies in human samples. It is therefore a preferred embodiment to detect human aSyn-specific antibodies, preferably human IgG or IgM antibodies, especially human IgG antibodies. As already mentioned, the detection of aSyn-specific antibodies in human is known in principle in the art; however, the role as a possible biomarker could not be verified. As shown with the present invention, this was also due to the analytical insufficiency of the detection methods available in the art. Due to the superiority of the method according to the present invention, the availability of these antibodies in human samples as biomarkers is enabled. The present method is therefore specifically suited to detect autoantibodies in biological samples. Accordingly, in a preferred embodiment of the present method, the aSyn-specific antibodies to be detected and quantified are autoantibodies.

In contrast to prior art methods, the present method uses aSyn-aggregates as probe for binding the aSyn-specific antibodies from the samples. Although such aggregates are known in principle in the art, it was not realised that the use of such aggregates in the analysis of aSyn-specific antibodies, especially in human samples, could significantly improve such methods, also in combination with the single particles detection techniques, such as FACS. Due to the use of such aggregates, the detection with single particles detection techniques (which are established techniques in various different fields and for different questions) is possible for analysing aSyn-specific antibodies in human samples (such as blood) which are usually very complex and difficult to handle.

Preferably, the dimensions of the aggregates to be used according to the present invention are standardised for analytical use. This can be done by establishing certain parameters during production of the aggregates. Depending on the conditions applied during generation of the aggregates, the size of the aggregates can be adjusted. Preferred sizes of the aSyn-aggregates according to the present invention are from 50 nm to 15 µm, preferably from 100 nm to 10 µm, especially from 500 nm to 5 µm (defined by the length of the aggregates (i.e. the longest extension).

A preferred method to provide aggregates suitable for the present invention comprises the step of incubating full length aSyn (1-140), naturally occurring splice variants including aSyn-98, aSyn 112 and aSyn-126 or modified full length aSyn including phosphorylated (especially at serin 129—Ser129), nitrosylated/nitrated, acetylated and mono-, di-, or tri-ubiquitinated aSyn, or C-terminally truncated forms of aSyn such as aSyn lacking the C-terminal 20-30 amino acids or even shorter aSyn proteins capable to form aggregates, at a pH of 2 to 9 for at least 20 min, preferably at least 1 h, especially at least 4 h. The duration of incubation is one of the parameters to adjust the size of the aggregates: the longer the incubation, the larger are the aggregates. Typical incubation times are from 10 min to 24 h. Shorter incubation times usually result in only very small aggregates and low number of aggregates; the aggregates produced with significantly longer incubation times than 48 h are usually not preferred in the present method. Of course, aggregates may also be sorted and "sieved" to arrive at the desired size, if needed, e.g. by fractionated centrifugation and similar techniques.

A preferred embodiment of the aSyn-comprising-aggregates according to the present invention relates to aggregates which—in addition to aSyn or an aSyn polypeptide—contains Aβ or a variant thereof. As for aSyn, only variants are used that allow aggregate formation. The following groups of Aβ variants are therefore specifically preferred in aSyn-comprising-aggregates (group 4 being the most preferred, followed by group 3, then group 2 and group 1)

Group 1 of Aβ variants: peptides containing either the core sequence Aβ16-20 or the second core sequence Aβ25-35. These peptides have been shown to form amyloid fibrils by themselves. Starting from these core sequences peptides can be extended by amino acids present in Aβ peptide or by alternative amino acids forming either truncated native Aβ peptides or truncated-modified Aβ peptides Group 2 of Aβ variants: peptides containing the sequence Aβ16-20-$X_{21-23}$-24-28-$X_{29-30}$-31-36 (meaning that aa 16 to 20, 24 to and 31 to 36 are present and linked by a 3 and a 2 aa linker (of arbitrary primary sequence)). Starting from this sequence peptide can be extended by amino acids present in Aβ peptide or by alternative amino acids forming either truncated native Aβ peptides or truncated-modified Aβ peptides Group 3 of Aβ variants: peptides containing the sequence Aβ16-36. Starting from this sequence peptide can be extended by amino acids present in Aβ peptide or by alternative amino acids forming either truncated native Aβ peptides or truncated-modified Aβ peptides Group 4 of Aβ variants: peptides containing the sequence Aβ11-36 or Aβp(E)11-36. Starting from this sequence peptide can be extended by amino acids present in Aβ peptide or by alternative amino acids forming either truncated native Aβ peptides or truncated-modified Aβ peptides.

Another preferred embodiment of the aSyn-comprising-aggregates according to the present invention relates to aggregates which—in addition to aSyn or an aSyn polypeptide—contains Tau protein or a variant thereof. As for aSyn (and Aβ), only variants are used that allow aggregate formation. Most preferred are aggregates of Tau, however, other aSyn-comprising-aggregates may comprise Tau with modified or truncated forms (e.g. Tau441 plus hyperphosphorylated Tau441 and/or shorter versions of Tau (e.g.: Tau 412, 410, 383, 381, 352), especially those that are naturally occurring in healthy or—especially—Tau protein variants that have marker function for a disease (either isoform of all 6 naturally occurring isoform or mutant forms thereof (e.g. P301L, P301S, V337M, etc.), e.g.: preferably simultaneously phosphorylated at amino acids 181, 202, 205, 212, 214, 231, 396 and, optionally, at additional residues present in Tau like 18, 153, 175, 199, 235, 262, 394, 404 and 422).

Another preferred embodiment of the aSyn-comprising-aggregates according to the present invention relates to aggregates which—in addition to aSyn or an aSyn polypeptide—contains islet amyloid polypeptide (IAPP) or a variant thereof. IAPP is synthesized as a 89 amino acid residue pre-prohormone. Cleavage of a signal sequence leads to a pro-IAPP containing 67 amino acids. The latter is further processed to the 37 residue mature IAPP. It has been shown that normal processing of pro-IAPP is a two-step process initiated by cleavage at its COOH terminus (likely by prohormone convertase 1/3 in the trans-Golgi network) followed by cleavage at its NH2 terminus (by prohormone convertase 2 in granules) to form the mature form of IAPP. IAPP is strongly conserved among mammalian species but exhibit notable variation between the amino acids 20 and 29. The differences in this region determine the ability of IAPP to aggregate and to form amyloids. In fact, species with one or more proline residues (except cats) at this region do not form islet amyloids. IAPP was discovered through its ability to aggregate into pancreatic islet amyloid deposits, which have been associated with β-cell dysfunction and death in Diabetes mellitus Type 2 (type 2 diabetes; T2D) patients and in other mammalian species like monkeys and cats. Amyloids are insoluble, fibrillar, protein aggregates with a β-pleated sheet structure. Amyloids have characteristic optical properties after staining with Congo red or thioflavin S and can be analyzed by light microscopy. However, the development of amyloid starts with the formation of fibrils or aggregates (7-10 nm in diameter and hundreds of nm in length) which can be detected by electron microscopy before evidence of amyloid is observed by light microscopy. In T2D patients, histological analyses of pancreatic tissue indicate that an accumulation of IAPP aggregates leads to the replacement of β-cell mass, resulting in progressive β-cell dysfunction and hyperglycemia. Besides that, IAPP fibrils appear to have a direct damaging effect on islets. Pancreatic amyloid deposits are found in more than 95% of type II diabetes patients and their formation is strongly associated with disease progression. In general, amyloids can form from proteins that fold to a compact tertiary structure in their unaggregated state, or they can originate from intrinsically disordered polypeptides that fail to adopt compact tertiary structures in their soluble native state. IAPP is an important example of intrinsically disordered polypeptide that forms amyloid in vivo. Although IAPP is major component of the islet amyloids in the pancreas of T2D patients, at least two additional elements have been identified in these deposits: apoE and the heparin sulfate proteoglycan perlecan (HSPGs). The kinetics of amyloid formation is complex and displays a sigmoidal profile characterized by a final steady state where soluble peptide is at equilibrium with amyloid fibrils. Amyloid formation can be accelerated by the addition of small amounts of pre-formed fibrils in a process called "seeding". A fraction of the IAPP that is secreted in T2D is incompletely processed. The impaired $NH_2$-terminal processing of pro-IAPP leads to amyloid formation and β-cell death. Accumulation of the $NH_2$-terminally extended human pro-IAPP intermediate (IAPP-Npro) may be a critical initiating step in amyloid formation. In fact, although IAPP-Npro was found to be less amyloidogenic in solution than mature IAPP, it interacts more effectively with glycosaminoglycans (GAGs), a component of HSPGs. Accordingly, IAPP forms with impaired $NH_2$-terminal processing, especially IAPP-Npro, are preferred forms in aSyn-comprising-aggregates according to the present invention.

Another preferred embodiment of the aSyn-comprising-aggregates according to the present invention relates to aggregates which—in addition to aSyn or an aSyn polypeptide—contains at least two further aggregate components in addition to aSyn or an aSyn polypeptide, especially one or more of Aβ or a variant thereof and/or one or more of Tau protein or a variant thereof and/or one or more of IAPP or a variant thereof.

Another preferred embodiment of the aSyn-comprising-aggregates according to the present invention relates to aggregates that comprise—besides aSyn or an aSyn variant as disclosed herein—an aggregate component of a different aggregate forming polypeptide species (as used herein, the term "polypeptide" is covering the term "protein" and usually these two terms are used synonymously; the term "protein" is therefore applied herein also for polypeptides with less than 100 or less than 50 amino acid residues). Preferably, this further aggregate-forming polypeptide species is selected from the group consisting of Tau protein or an aggregate-forming variant thereof, Aβ1-42 peptide or an aggregate-forming variant thereof; IAPP and an aggregate-forming variant thereof, especially IAPP-Npro, TAR-DNA binding protein 43 (TDP43) or an aggregate-forming variant thereof; and Superoxide-Dismutase 1 (SOD1) or an aggregate-forming variant thereof.

As already stated, preferred aggregate forming variants of Tau ("Tau variants") are hyperphosphorylated Tau, abnormally phosphorylated Tau (as referred to and defined in Shahani et al. J. Neurosci. 26 (2006), 6103-6114), Tau protein variants that have marker function for a disease (either isoform of all naturally occurring isoforms (Tau441, Tau412, Tau410, Tau383, Tau381, Tau352) or mutant forms thereof (e.g. P301L, P301S, V337M, etc.), e.g.: forms preferably simultaneously phosphorylated at amino acids 181, 202, 205, 212, 214, 231, 396 and, optionally at additional residues present in Tau like 18, 153, 175, 189, 235, 262, 394, 404 and 422, of Tau441, Tau412, Tau410, Tau383, Tau381, Tau352 (a more detailed analysis of Tau phosphorylation is disclosed e.g. in Hanger et al., Trends in Mol. Med. 15 (2009), 112-119).

According to the present method, the samples wherein the aSyn-specific antibodies are to be detected are contacted with the aSyn-aggregates to achieve binding of the aSyn-specific antibodies possibly present (and reactive vis-a-vis aSyn-aggregates) in the samples. The concentration of the aSyn-aggregates has therefore to be adjusted in order to provide enough binding positions for the antibodies. Accordingly, the concentration of the aSyn-aggregates for binding the antibodies in the sample is preferably in the range of 0.01 to 10 μM, preferably 0.1 to 1 μM. The optimal concentration is also dependent on the nature of antibodies to be bound, the nature of the sample, the planned contact time and the size of the aggregates.

The present method is mainly aimed for application on human samples. It is therefore preferred that biological sample is human blood or a sample derived from human blood, preferably human serum or human plasma; human cerebrospinal fluid or human lymph. With such sample sources, also serial and routine testing may be established (especially for samples derived from blood).

Preferred contact times which allow proper binding of the antibodies in the sample to the aggregates are at least 10 min (e.g. 10 min to 48 h), preferably from 15 min to 24 h, especially from 30 min to 2 h.

If the biological sample is not specifically pre-treated, the aSyn-specific antibodies which have a binding capacity to the aSyn-aggregates will be bound during contact with the aSyn-aggregates. The aSyn-specific antibodies which are masked in the sample (i.e. those antibodies which are already bound to a binding partner (e.g. an aSyn-comprising structure, or endogenous aSyn peptides)) will not be detected by the method according to the present invention (absent such specific sample pre-treatment). Whereas the identification and quantification of only reactive antibodies will in many cases be sufficient and desired, there may be situations or diagnostical questions where the total amount of aSyn-specific antibodies in the sample should be detected (reactive and unreactive) or all, the number of reactive aSyn-specific antibodies, the unreactive ("masked") and the total number of aSyn-specific antibodies.

Therefore, according to another preferred embodiment of the present invention, the samples are demasked, i.e. the aSyn-specific antibodies are "freed" from any binding to binding partners present in the sample previous to the contact with the aSyn-aggregates according to the present invention. This allows detection of all aSyn-specific antibodies in the sample and not only detection of those antibodies which are not bound to a binding partner in the sample ("free" or "reactive" antibodies). In the course of the present invention it was determined that the amount of reactive aSyn-specific antibodies, especially reactive aSyn-specific IgG, was a key marker for the diagnosis and development of PD and MSA. The present method is, as stated above, also suitable for determining the overall amount of aSyn-specific antibodies in a sample, i.e. the free (or "reactive") antibodies as well as those antibodies which are already bound (e.g. to aSyn structures) in the sample. This can be helpful in establishing the difference (Δ) of reactive vs. non-reactive antibodies in a sample, a parameter which is also of significant importance for PD and MSA diagnosis. Whereas such difference is not present (or low) in persons with "healthy status" concerning PD and MSA, this difference is crucial for the marker function in PD and MSA, concerning both aSyn-specific IgG and aSyn-specific IgM.

The method according to the present invention applies a single particle detection technique. Such techniques allow identifying and quantifying ("count") the number and amount of "positive" binding results of the aSyn-specific antibody to the aSyn-aggregates. A preferred embodiment of this technology is FACS which is an established technique in the present field. Other detection methods to be used to detect the antibodies bound to the aSyn-aggregates are e.g. Luminex or mass cytometry.

According to the Luminex technology, sample preparation may be performed as described in Material and Methods. Following sample preparation aSyn-aggregates recognized by specific aSyn-specific antibodies may be detected by a secondary antibody coupled to fluorescent-dyed microspheres which can be detected in multiplex detecting systems e.g. a Luminex reader (Binder et al., Lupus15 (2005): 412-421).

If mass cytometry is used as single particle detection technique, sample preparation may also be performed as described in Material and Methods of the example section below. Sample preparation is done as described. Following sample preparation aSyn-aggregates recognized by specific Abs may be detected by a secondary antibody coupled to stable isotopes of transition elements which can be detection by atomic mass spectrometry. The sample can then be sprayed through an argon plasma filled inductive coil heated to a temperature of >5,500 K. The sample is vaporized and ionized into its atomic constituents, and the number of the isotope-tagged antibody is quantified by time-of-flight mass spectrometry (Janes et al., Nat. Biotechnol. 29 (2011): 602-604).

Alternatively it is also possible to apply single particle detection techniques where one binding partner (aSyn-aggregates or antibody/serum) is immobilized but binding is measured under flow conditions. Examples are the Hybcell-technology and the Surface Plasmon Resonance technology. Using the Hybcell technology in the present invention, serum samples can be spotted on the surface of the Hybcell (a rotating cylinder) and incubation can be performed with directly fluorescence-labelled preincubated aSyn-aggregates or alternatively with a fluorescence-labelled monoclonal aSyn-specific second antibody. Antibodies bound to aSyn-aggregates are detected with a laser (Ronacher, Anagnostics Technical Note ANA-TN-005 (2010)). If Surface Plasmon Resonance is used in the method according to the present invention, a reverse setup can be applied: the preincubated aSyn-aggregates can be immobilized on a chip surface. The binding of aSyn-specific antibodies from serum to the aSyn-aggregates on the chip can be detected by increase of mass on the chip surface and therefore no labelling of the binding partners is necessary. To increase sensitivity or determine IgG-subtypes a serial injection of anti-IgG-AB is possible (Cannon et al., Anal. Biochem. 328 (2004): 67-75). Instead of directly immobilizing aSyn-aggregates to the chip surface a capture antibody can be used. For this setup an aSyn-specific antibody is immobilized on the chip surface followed by the injection of preincubated aSyn-aggregates. After the capturing of the aggregates serum is injected and reactivity is measured by increase of mass.

Detection of the binding of aSyn-specific antibodies to the aSyn-aggregates according to the present invention can be performed by any suitable method known e.g. Fluorescence Spectroscopy (Missailidis et al., Methods in Molecular Biology 248 (2003): 431-441) for detecting the aSyn-specific antibodies bound to the aSyn-aggregates by a secondary antibody (e.g. a secondary labelled anti-IgG- or anti-IgM-antibody).

Detection of autoantibodies bound to aggregates can also be performed using substrates specifically binding antibodies such as Protein A or Protein G. Another possibility is to precipitate aSyn-aggregate specific autoantibodies using the aSyn-aggregates, wash the complex and biotinylate the antibodies. Subsequently streptavidin can then be used as second step reagent.

In contrast to prior art disclosures (e.g. in WO 2010/099199 A1, WO 2010/069603 A1, and EP 2 366 714 A1), wherein proteins, such as aSyn, Tau, Aβ or variants thereof are immobilised on particles (such as nanoparticles, nano or microbeads, etc.), the aggregates according to the present invention are provided without such surfaces but consist of the aggregates as such without any scaffold or surface aids. This resembles the natural situation, especially in human blood, more closely than with micro- or nanobeads.

A preferred field of use of the present invention is the diagnosis of Synucleinopathies, including Parkinson's disease (PD), Lewy Body Disease (LBD), Dementia with Lewy Bodies (DLB), Parkinson's Disease Dementia (PDD), Multiple System Atrophy (MSA), Pure Autonomic Failure (PAF), REM Sleep Behaviour Disorder (RBD), Neurodegeneration with Brain Iron Accumulation type I (NBIA Type I) and inclusion body myositis (IBM); as well as other diseases, such as Alzheimer's disease (AD) and Down Syndrome (DS), Progressive Supranuclear Palsy (PSP), Cortico-basal degeneration (CBD), Frontotemporal Dementia/Pick's Disease (FTD/PiD).

A preferred embodiment of the present invention is the diagnosis of proteinopathies that is significantly improved by the present invention. Proteinopathies are diseases, especially neurodegenerative diseases that are caused by a malformed protein. Preferred proteinopathies to be diagnosed according to the present invention are Alzheimer's disease (AD), Dementia in Down's Syndrome, Parkinson's disease (PD), Lewy Body Disease (LBD), Dementia with Lewy Bodies (DLB), Parkinson's Disease Dementia (PDD), Multiple System Atrophy (MSA), Pure Autonomic Failure (PAF), REM Sleep Behaviour Disorder (RBD), Neurodegeneration with Brain Iron Accumulation type I (NBIA Type I), inclusion body myositis (IBM), Cortico-Basal Degeneration (CBD), Progressive Supranuclear Palsy (PSP), Pick's Disease (PiD), Dementia pugilistica (chronic traumatic encephalopathy, DP), Frontotemporal dementia (FTD), Lytico-Bodig disease (LD), Huntington's disease (HD) and Spinocerebellar ataxias (Type 1, 2, 3 and 7) and Amyotrophic lateral sclerosis (ALS), prionosis and type II diabetes; and diseases with alpha synuclein deposition and/or aggregation, especially Alzheimer's disease (AD) Down Syndrome (DS), Progressive Supranuclear Palsy (PSP), Corticobasal degeneration (CBD), Frontotemporal Dementia/Pick's Disease (FTD/PiD); especially for tracking early stages of the proteinopathy and for observing the development of clinical trials for drugs for the treatment of proteinopathies.

The present method is specifically suited for using in connection with PD and MSA diagnosis. With the present invention, aSyn-specific autoantibodies in human patients are provided as markers for PD and MSA status. People with "normal" level of aSyn-specific antibodies in their blood are "healthy" with respect to PD and MSA. If this level is modified in a patient with PD and MSA or subjects with a risk of developing PD and MSA or being suspected to have PD and MSA, such modification level correlates with PD and MSA. A "modified" level may be a modification of the absolute number of the aSyn-specific antibodies or a modification of the reactivity of the totality of the aSyn-specific antibodies (e.g. of a given class of aSyn-specific antibodies (IgG, IgM, etc.). For example, modified reactive aSyn-specific IgG correlates with and is a marker for PD and MSA. With the present method, when the "healthy" level of reactive aSyn-specific IgG is set to 100%, a significant modification in reactive aSyn-specific IgG, is e.g. a decrease to 70% and lower, to 50% and lower or to 30% and lower, or an increase of at least 30%, e.g. at least 50% or at least 100%, in a blood sample.

Since the present invention provides a marker for PD and MSA and even for the development of PD and MSA, it is possible to use this method for observing the development of the disease and the performance of possible treatment methods, especially whether the method of treatment enables to establish "healthy" or "healthier" levels of Aβ-specific antibodies, especially IgG or IgM.

The present method is therefore preferably used for the monitoring of PD and MSA patients, especially PD and MSA patients who are treated with medicaments for curing or ameliorating PD and MSA. The present method can be successfully applied for observing patients in clinical trials for PD and MSA vaccines (e.g. PD01A, Trial AFF008, NCT 01568099) or aSyn-targeting disease-modifying drugs.

The method according to the present invention can also be used for evaluating the risk of developing a proteinopathy, preferably a synucleinopathy, especially PD and MSA, or for detecting early stage of a proteinopathy, preferably a synucleinopathy, especially PD and MSA. With the present invention, it is in principle made possible to detect changes in the immunological set-up of patients with respect to aSyn-specific autoantibodies at a significantly earlier point in time than cognitive and/or functional impairments. This could allow a significant improvement of early diagnosis of a proteinopathy, preferably a synucleinopathy, especially PD and MSA, with respect to a much larger part of the population if established in routine testing format. This makes patients eligible for early stage treatment regimens and/or prevention (or delay) strategies for proteinopathies, preferably synucleinopathies, especially PD and MSA, especially immunotherapy (including vaccination).

According to another aspect, the present invention relates to a kit for performing the method according to the present invention comprising aSyn-comprising-aggregates, and a sample container, especially for human samples (e.g. blood, serum, plasma).

Preferably, the kit according to the present invention may further contain means for detecting aSyn-comprising-aggregates being bound to aSyn-specific antibodies, preferably secondary antibodies, especially labelled secondary antibodies, e.g. anti-IgG- or anti-IgM-antibodies). Further components can be standard samples, positive and/or negative controls, instructions for use and suitable packaging means (e.g. stable boxes, coloured vials, etc.).

The present invention is further illustrated by the following examples and the drawing figures, yet without being restricted thereto.

FIG. 1 shows the size determination of aSyn-aggregates using FACS-analysis. aSyn-aggregates can be detected using flow cytometry and are depicted as a homogenous population in the SSC-A (log-scale)—and FSC-A (log-scale) channel in the dot blot (A). The size distribution (defined by FCS-A signal) of aSyn-aggregates was determined using commercially available calibrated size beads (1, 2, 4, 6, 10, and 15 µm) as shown in FSC-A-histogram (B).

Figure 2:
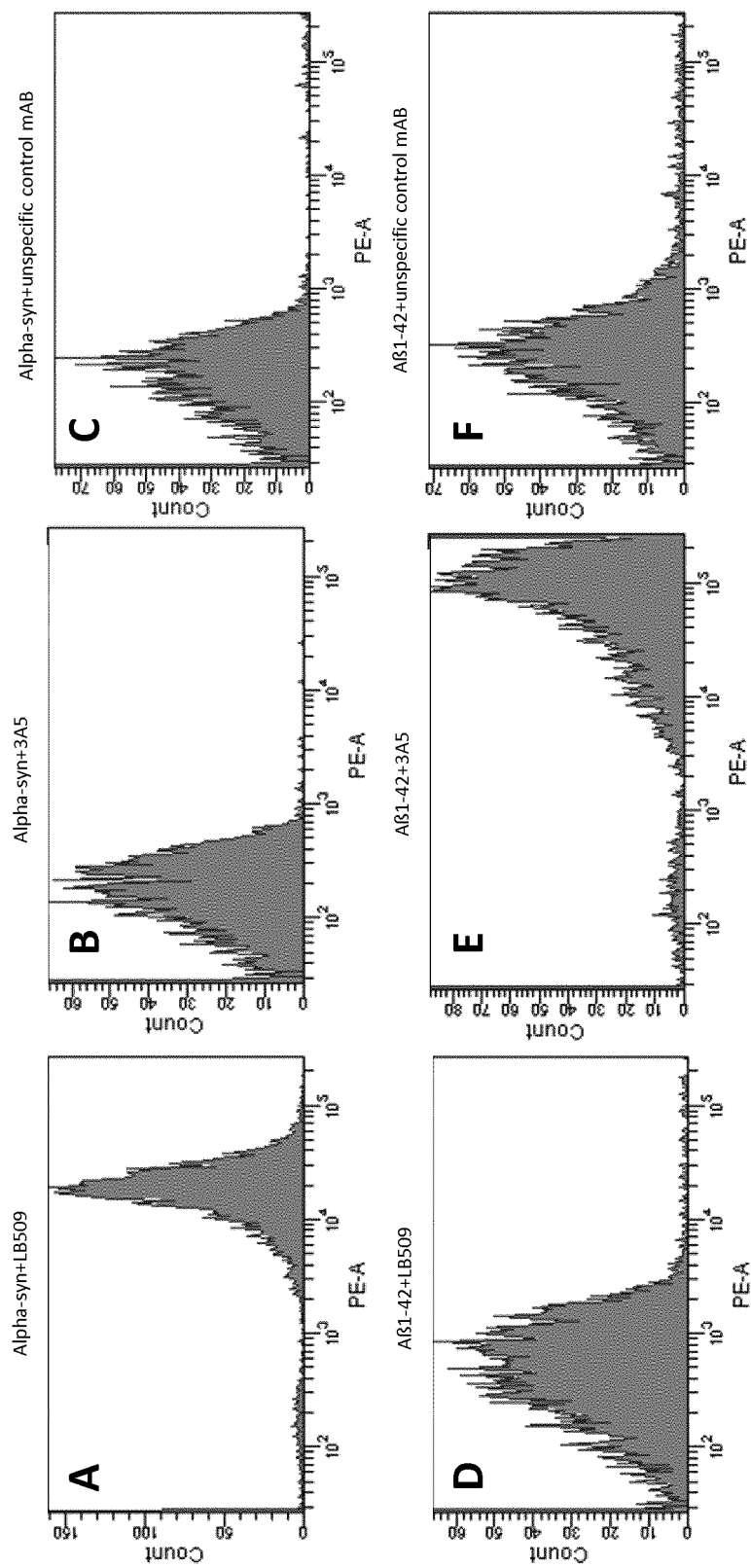

FIG. 2 shows the detection of monoclonal antibody reactivity to aSyn-aggregates (A, B, C) and Aβ1-42 aggregates (D, E, F) using the FACS-based assay. The aSyn-specific monoclonal antibody LB509 binds specifically to aSyn aggregates (A) but does not interact with Aβ1-42 aggregates (D). In contrast the Aβ1-42 specific antibody 3A5 binds Aβ1-42 (E) but not aSyn aggregates (B). Reactivity was determined using a secondary anti immunoglobulin-PE-labelled antibody in FL2-PE-channel.

An irrelevant control mAb D129 neither interacts with aSyn (C) nor with Aβ1-42 (F) aggregates indicating the finding that different aggregates bind specifically respective mAbs (E). Fluorescence intensity as shown in C and F are comparable with background staining as seen when aggregates are incubated with PE-labelled secondary antibody alone.

Figure 3:
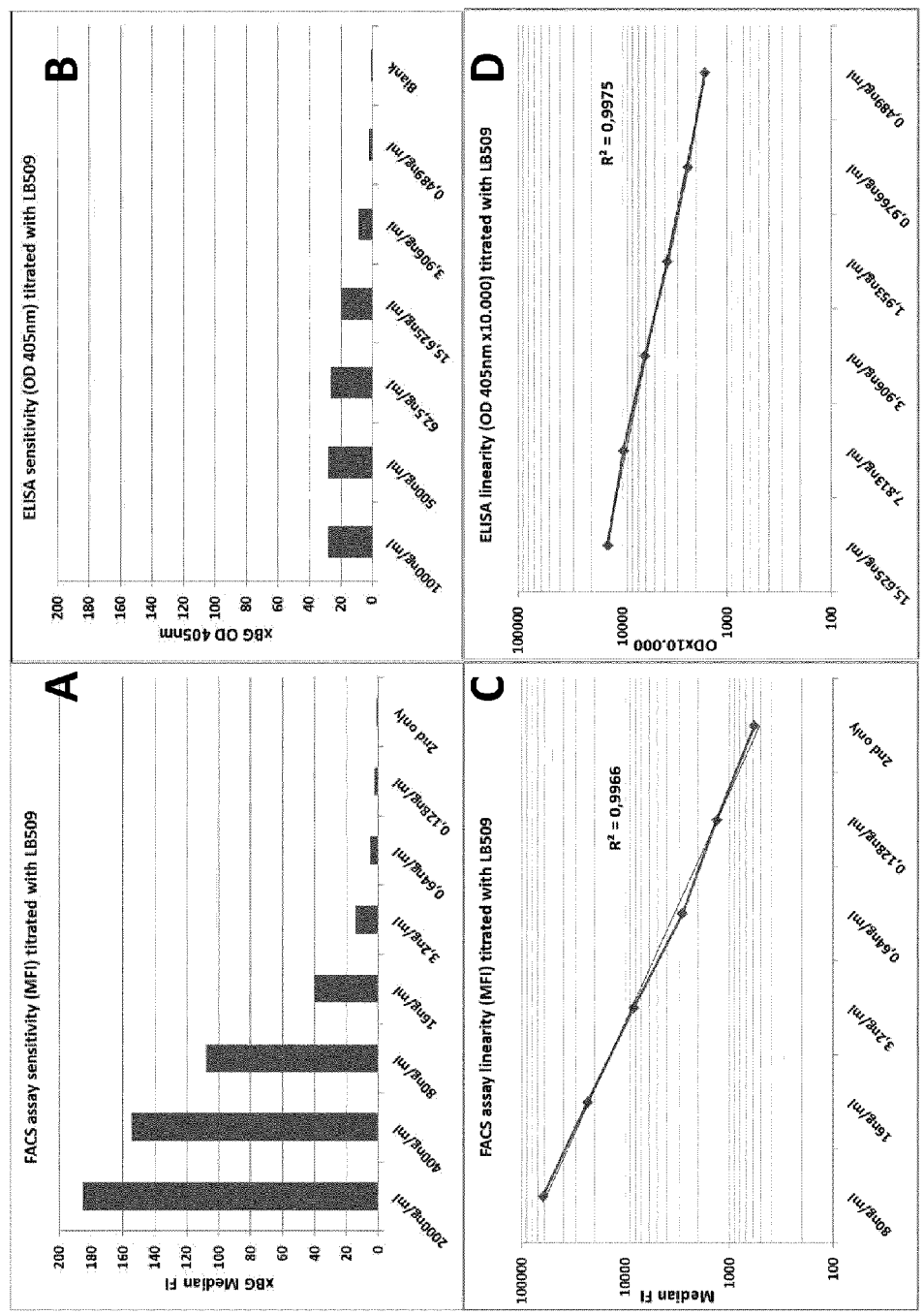

FIG. 3 shows the comparison of assay sensitivity (A, B) and assay linearity (C, D) for two different methods, the FACS-based method (A, C) and ELISA (B, D). (A) aSyn aggregates were incubated with a dilution series of mAb LB509 and reactivity was determined in FL-2 channel using flow cytometry. (B) mAb LB509 titration on Maxisorp ELISA plates coated with aSyn. Please note that for comparison all results are given in fold-background signal.

Lower panels show the linear range of the herein described FACS aggregation assay (C) and ELISA (D). The linear range was determined with the aSyn specific mAB in the FACS aggregation assay ranging from 80 ng/ml to 0.128 ng/ml (over three log-stages) and in the ELISA ranging from 15.625 ng/ml to 0.498 ng/ml (over two log-stages). The black lines represent the trend line calculated in Excel for the indicated range. The Pearson's coefficient of determination ($R^2$) is indicated for both titrations.

Figure 4:
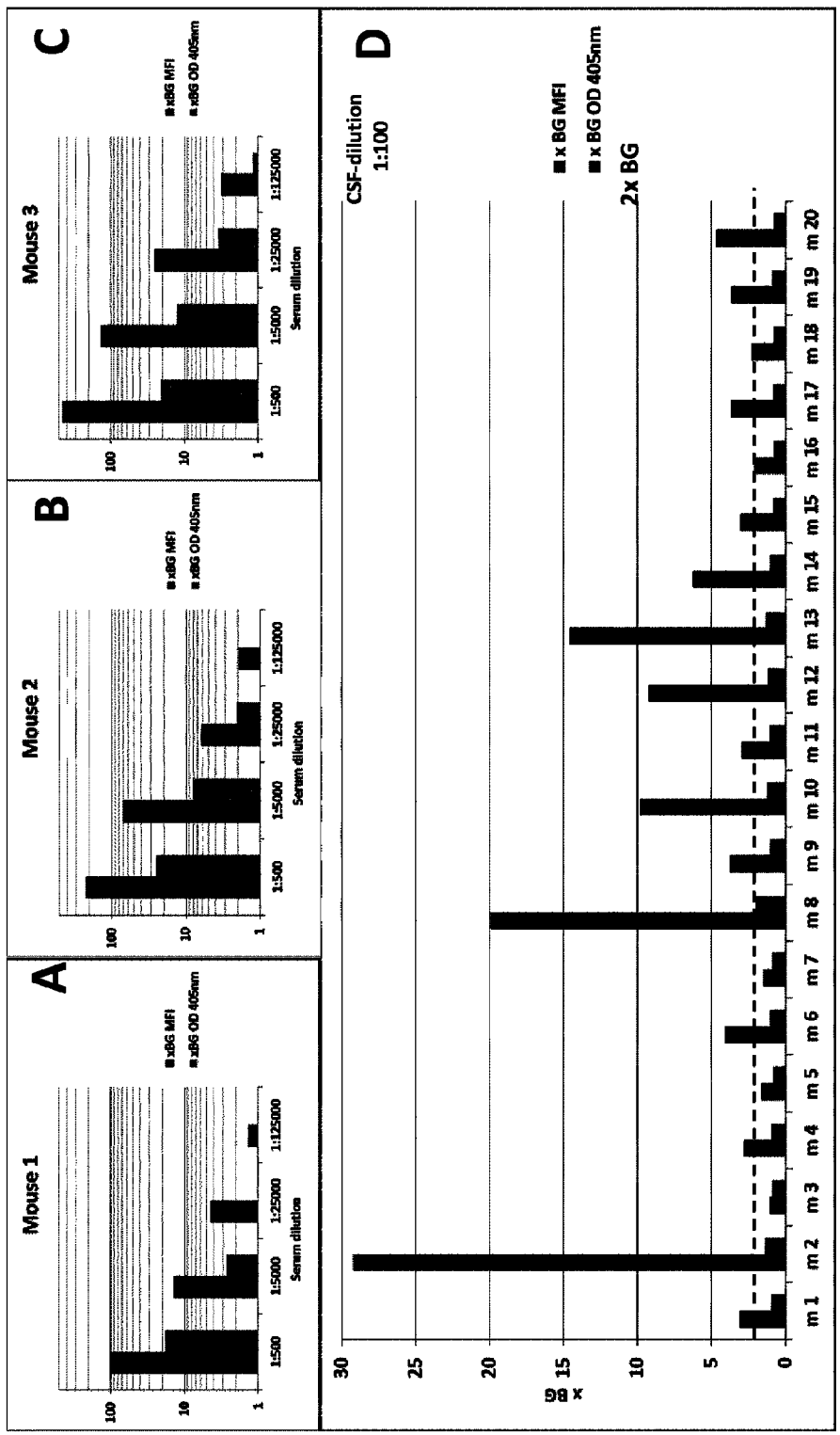

FIG. 4 shows signals derived from aSyn FACS aggregation assay (black bars) and aSyn ELISA (grey bars) using different dilutions of sera derived from individual mice (A, B, C), or using a 1:100 dilution of CSF derived from 20 individual mice (D) immunised with aSyn specific vaccine. All values are depicted as fold background values.

As can be seen the FACS aggregation assay detects aSyn specific antibodies with up to 30-fold higher sensitivity than standard methods such an ELISA.

Sera from mouse 2 (B) and 3 (C) showed a MFI signal above 2×BG even at a dilution of 1:125,000 and sera from mouse 1 (A) resulted in MFI>2×BG at a dilution of 1:25,000, whereas no signals could be detected in ELISA with indicated dilutions.

Using sera dilutions of 1:500 the MFI signals reached more than 400 times background (C) whereas in the ELISA system the same serum dilution resulted only in a background increase of 20 fold.

Comparison of the two methods with a 1:100 dilution of the CSF samples resulted in only one out of 20 samples reaching asignificant signal detection in ELISA. 17 out of 20 samples showed a MFI signal>2×BG when measured in the FACS aggregation assay.

Figure 5:
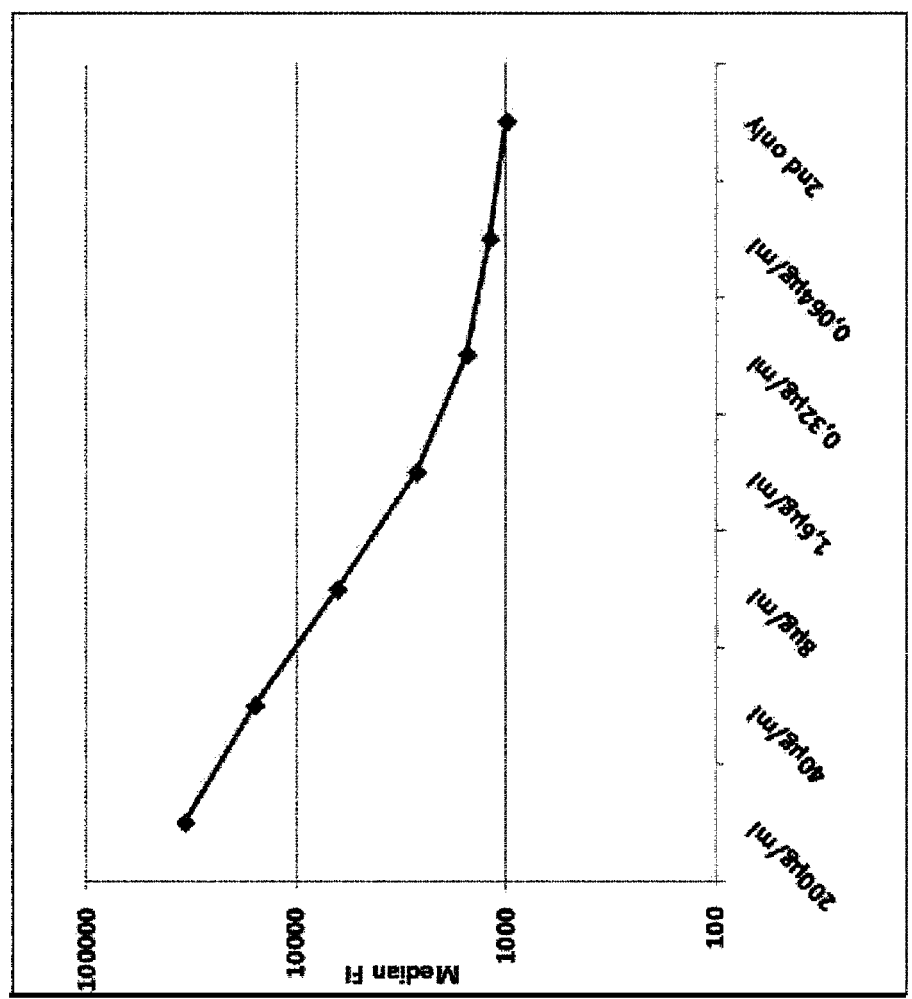

FIG. 5 shows the determination of aSyn-specific IgG auto-antibody reactivity in a human preparation of IgG fraction (IVIG) which is extracted from plasma derived from healthy donors. IVIG was subjected to the described FACS assay. Fluorescence intensity of Aβ-aggregates was evaluated in FL2-PE channel and is expressed as Median Fluorescence Intensity (MFI).

Figure 6:
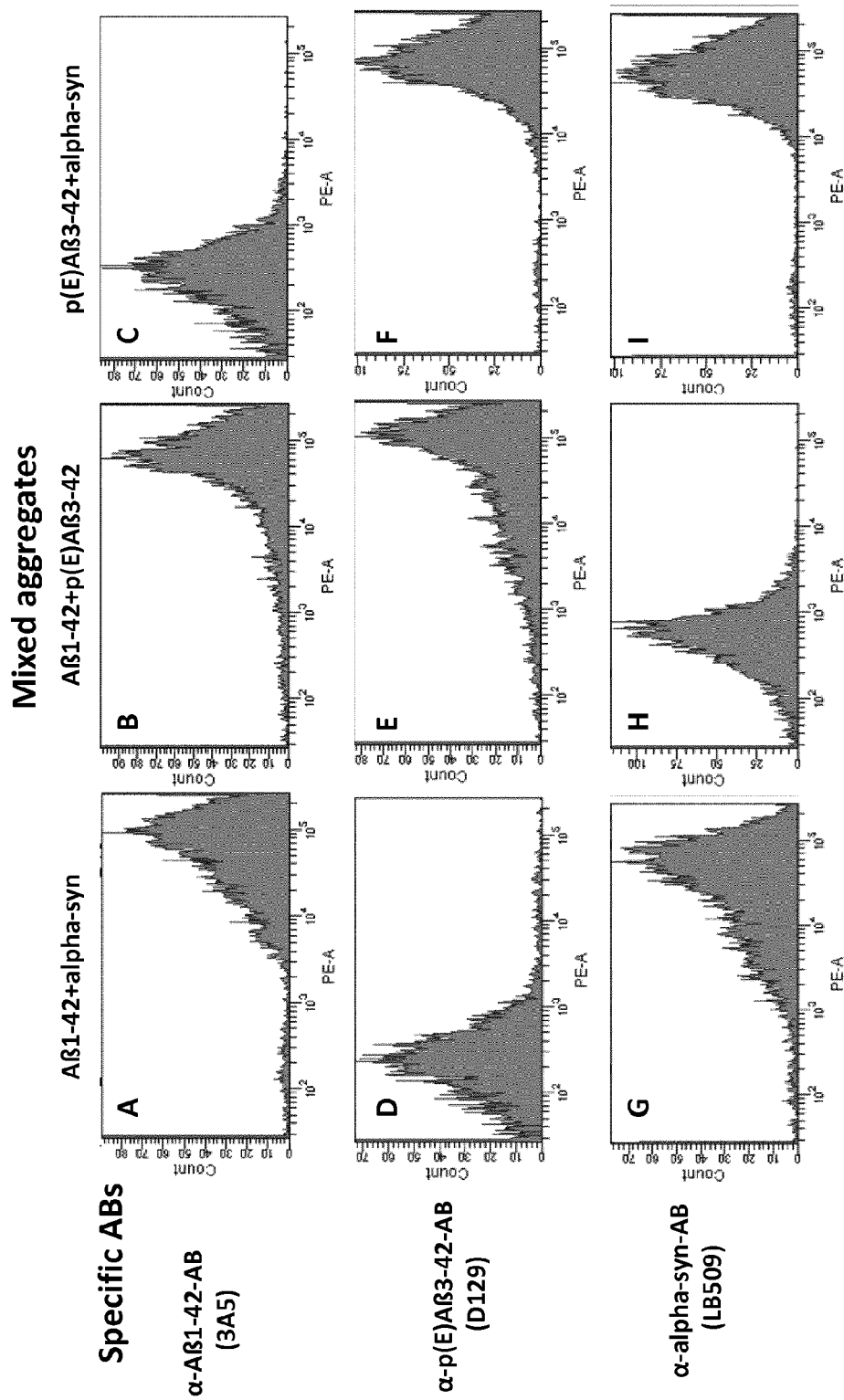

FIG. 6 shows the reactivity of mAB against aggregates generated from equimolar mixtures of either aSyn with Aβ1-42, aSyn with p(E)Aβ3-42 or Aβ1-42 with p(E)Aβ3-42. Aggregates were incubated with monoclonal antibodies specific either for Aβ1-42 (3A5) p(E)Aβ3-42 (D129) and aSyn (LB509) and the mAB-binding pattern of the mixed aggregates was determined.

FACS PE-histograms show that the monoclonal antibody 3A5 binds exclusively mixtures which contain Aβ1-42 aggregates (6A+B) but no reactivity to the p(E)Aβ3-42/aSyn aggregate mixture (6C). The anti-p(E)Aβ3-42mAB D129 binds only mixtures that contain p(E)Aβ3-42 (6E+F) but shows no reactivity to Aβ1-42/aSyn (6D). The aSyn specific mAB LB509 reacts only with aggregate mixtures containing aSyn (6G+I) but does not react with the Aβ1-42/p(E)Aβ3-42 aggregate mixture (6H).

Figure 7:
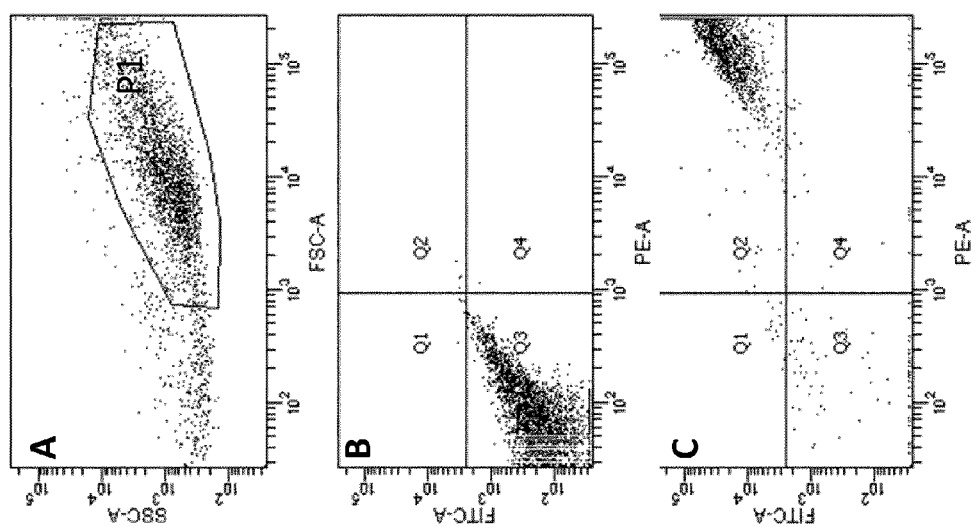

FIG. 7: FACS analysis of aggregates generated with equimolar mixtures of differentially fluorescent-labelled Aβ1-42 and aSyn peptides of Aβ1-42-Hilyte-555 (PE) and aSyn-Hilyte-488 (FITC). Acquired aggregates with a size range of 0.5-10 μm were gated in P1 in the FSC-A/SSC-A (A) and P1 was further evaluated in the PE/FITC-dot plot to determine the contribution of Aβ1-42-Hilyte-555 (PE) and aSyn-Hilyte-488 (FITC) (C). Unlabelled mixed-aggregates were used as negative control (B).

Figure 8:
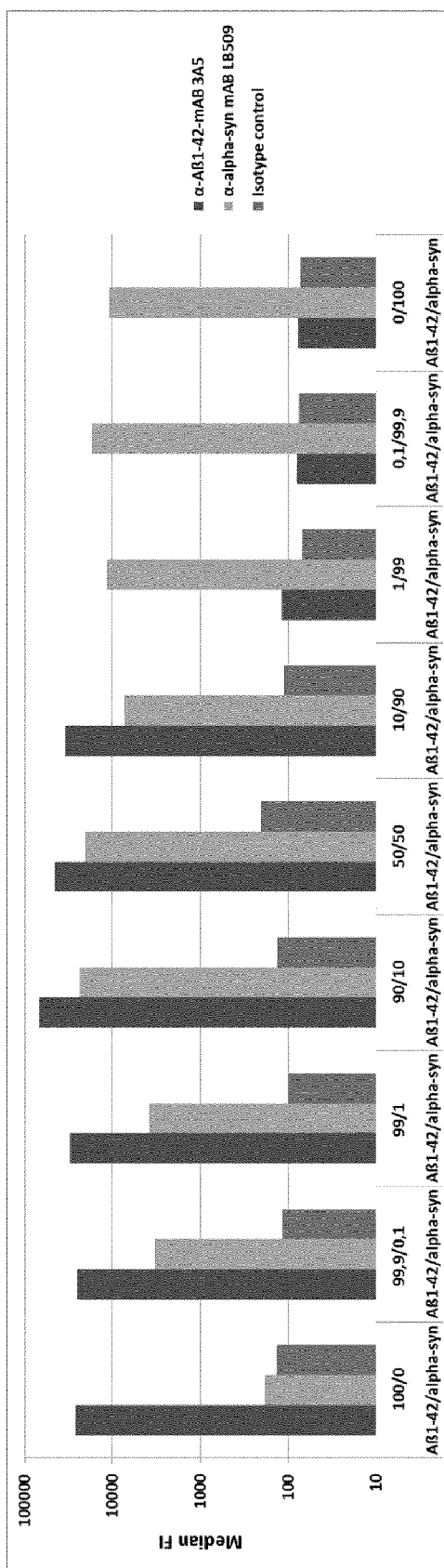

FIG. 8: mAB reactivity against aggregates generated from different concentrations of aSyn and Aβ1-42. Aβ1-42 and aSyn peptides were mixed as indicated in table 1.

Figure 9:
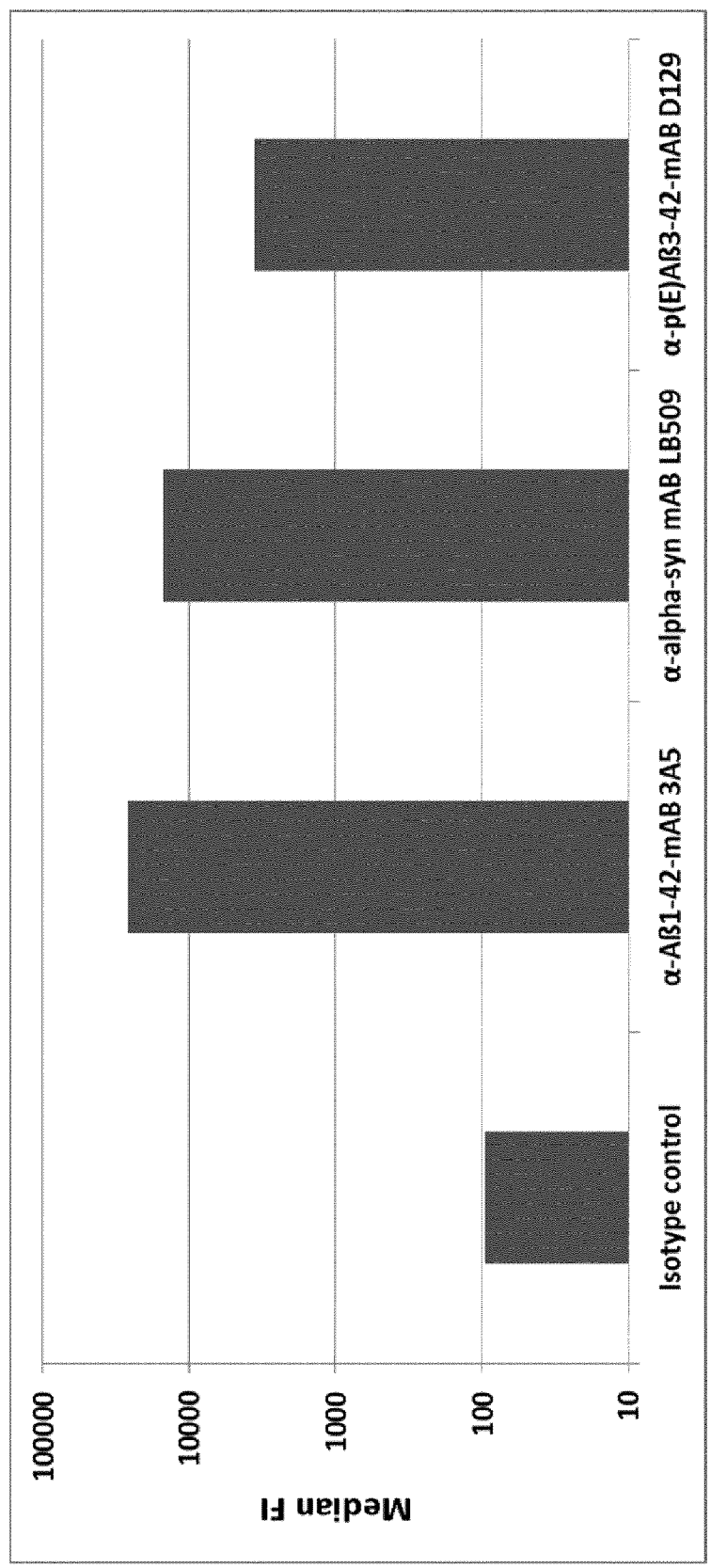

FIG. 9 shows the reactivity of mAbs specific for Aβ1-42 (3A5), Aβp(E)3-42 (D129) and aSyn (LB509) against aggregates composed of an equimolar mixture of Aβ1-42, Aβp(E)3-42 and aSyn peptides.

Figure 10:
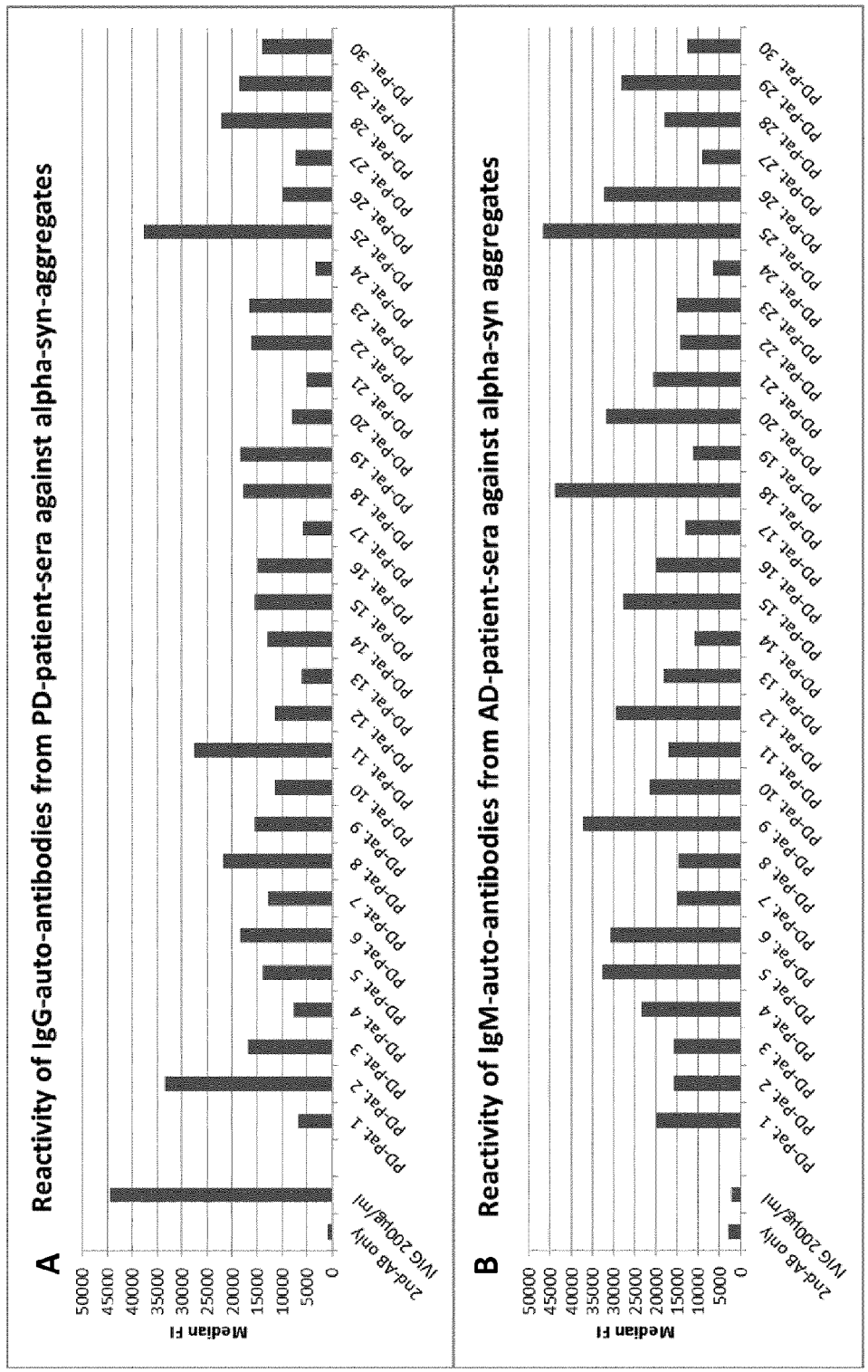

FIG. 10 shows the determination of IgG (A) and IgM (B) auto-antibody reactivity in human plasma derived from PD patients. Plasma samples (dilution 1:300) was subjected to the described FACS assay. Fluorescence intensity of binding to aSyn-aggregates was evaluated in FL2-PE channel and is expressed as Median Fluorescence Intensity (MFI).

EXAMPLES

Materials and Methods

Detection of aSyn-Specific Antibodies Using ELISA aSyn peptide (purchased from Anaspec) was diluted in 100 mM NaHCO$_3$ (pH 9.2) at a concentration of 5 μg/ml and coated on Maxisorp 96-well plates overnight. To prevent unspecific binding plates were blocked using 1% BSA/PBS at 37° C. for 1 h. The ELISA was performed with a serial dilution of mAbs (starting with indicated concentration) in binding buffer (PBS/0.1% BSA/0.1% Tween20) at 37° C. for 1 h. After repeated washing steps (3×) with PBS/0.1% Tween20 the secondary anti-human Ig HRP (0.5 μg/ml) detection-antibody was added for 1 h at 37° C. Samples were washed again 3× and ABTS (0.68 mM in 0.1 M citric acid pH 4.3) was added for 30 min for assay development before OD-measurement on plate reader (Biotek—Gen5 Program) at wave length 405 nm.

Detection of aSyn-Specific Antibodies Using FACS Analysis

500 μg of lyophilized aSyn was dissolved in 100 μl of sterile filtered MonoQ by resuspending and short vortexing until solution was clear. Subsequently this solution was sonicated for 30 sec in a sonication water bath and stored in 5 μl aliquots at −20° C. without shock-freezing. To induce the formation of aggregates, aliquots were thawed and the entire volume of the aSyn solution was incubated at a concentration of 35 μM in 1% NH4OH (pH4.5) at 37° C. on shaker (350 rpm) overnight in an Eppendorf tube. aSyn aggregates were used for one experiment only and residuals were discarded.

Additionally, the amount of aggregates was determined to ensure comparable aSyn-aggregate density before sample preparation for every experiment.

The number of generated aggregates after overnight incubation was measured in the FSC/SSC channel before sample preparation and the number of aggregates used as a substrate was normalized. In detail 3 μl of overnight generated aSyn-aggregates were diluted in 97 μl of 0.5% BSA/PBS as described above. 3 μl represent the standard amount of substrate used for each sample. Using the FACS Canto II, 70 μl of this aSyn-dilution was measured at high flow rate (2 μl/s) resulting in an acquisition time of 35 seconds and the number of aggregates was determined. Approximately 10.000 particles acquired under these conditions were defined as standard. If more or less aggregates were detected, the volume of aSyn-aggregate solution used as a substrate for further sample preparation was adjusted to ensure comparable aggregate density within samples in different experiments. This means that if for example only 5000 events were acquired the volume of substrate for sample preparation was increased to 6 μl per well. As indicated above ~10.000 particles were used as starting material for each sample preparation.

For the detection of aSyn-specific antibodies 3 μl of the aSyn-aggregate suspension were mixed with 92 μl of 0.2 μm filtered 0.5% BSA/PBS and subsequently transferred into a well of a 96-well V-shaped bottom plate for further sample preparation. These suspensions were incubated for 60 min at RT for blocking.

Aliquots of murine or human serum samples from −80° C. were thawed freshly for each measurement, diluted 1:50 in case of murine serum samples or diluted 1:5 in case of human serum samples in 0.5% BSA/PBS and subsequently these samples were 0.2 μm filtered by centrifugation (3000 rpm for 3 min) through 0.22 μm 96-well-filter plates in a 96-well plate-centrifuge. CSF samples were prediluted 1:5 in 0.5% BSA/PBS and were not sterile filtered. 5 μl of pre-diluted serum- or CSF-samples were added to 95 μl of the aSyn-aggregate-suspension resulting in final murine serum dilution of 1:1000 and a human serum or CSF dilution of 1:100. After 60 min incubation at RT on a shaker (450 rpm) 150 μl of 0.5% BSA/PBS was added to every well. The plate was centrifuged for 5 min at 3000 rpm (96-well plate-centrifuge) and the supernatant (SN) was removed by thoroughly pouring it into the sink. Thereafter, 200 μl of 0.5% BSA/PBS was added and this washing step was repeated 3 times. For the detection of murine serum and CSF samples after the 4th washing step the SN was discarded again and pellet was re-suspended in 100 μl 0.5% BSA/PBS containing a 1:10.000 dilution of anti-mIgG (H+L) F(ab')$_2$ Fragment labeled with PE (Jackson Immuno Research). For detection of IVIG a 1:1000 dilution of anti-hIgG (H+L) F(ab')$_2$ Fragment labeled with PE (Jackson Immuno Research) was used. Samples were incubated for another 60 min at RT on a shaker (600 rpm). Subsequently, samples were measured on a FACS Canto equipped with a high-throughput sampler (HTS) without an additional washing step. aSyn aggregates were identified based on their FSC/SSC characteristics. The signal of Abs binding to the aggregates was assessed in FL2-PE channel and was evaluated based on its median fluorescence intensity (MFI) using FACS Diva software.

Generation and Detection of Mixed Aggregates

To test whether different peptides (e.g. aSyn and Aβ1-42) form mixed aggregates containing both peptides fluorescent N-terminally-labelled Aβ1-42 and C-terminally labelled aSyn peptides were used. As described by Anderson and Webb (BMC Biotechnology 2011, 11:125) labelling of Aβ and aSyn peptides does not prevent amyloid aggregate formation. Therefore, Aβ1-42-Hilyte-555 (detectable in the PE-channel) and aSyn-Hilyte-488 (detectable in the FITC-channel) were mixed at equimolar ratio (20 μM) and incubated for 20 h at room temperature on shaker (350 rpm) in 1% NH4OH (pH 4.5). After incubation these aggregates were analysed using the FACS Canto II. Acquired aggregates were gated for size in P1 (~0.5 μm-10 μm) in the FSC-A/SSC-A and P1 was further analysed in the PE/FITC-dot plot to determine the distribution of Aβ1-42-Hilyte-555 (PE) and aSyn-Hilyte-488 (FITC).

Detection of Specific Antibody Reactivity by FACS Analysis Using Aggregates Generated from Mixed Solutions of Monomeric aSyn, Aβ1-42 and p(E)Aβ3-42 Proteins as a Substrate 500 μg of lyophilized aSyn or 100 μg of either Aβ1-42 or p(E)Aβ3-42 was dissolved in 100 μl of sterile filtered MonoQ (aSyn) or 100 μl of sterile filtered 1% NH4OH pH11 (Aβ1-42 and p(E)Aβ3-42) by resuspending and short vortexing until solution was clear. Subsequently these solutions were sonicated for 30 sec in a sonication water bath and stored in 5 μl aliquots at −20° C. without shock-freezing. To induce the formation of aggregates, aliquots from individual proteins were thawed and the entire volume of the three individual protein solutions were diluted to an equimolar concentration of ~35 μM in 1% NH4OH (pH4.5). These protein solutions were mixed in all three possible combinations before incubation at 37° C. on shaker (350 rpm) for 20 h in an Eppendorf tube as follows: Aβ1-42 & aSyn, Aβ1-42 & p(E)Aβ3-42 and p(E)Aβ3-42 & aSyn. Furthermore, not only equimolar ratios (=50:50) but also a titration experiment to test different ratios of aggregate mixtures was performed. The ratios of aggregate mixes are indicated in the experiment (e.g. 1:100=1 μl aSyn (20 μM)+99 μl of Aβ1-42 (20 μM) solution). Mixed aggregates were used as substrates for further sample preparation and were treated as described for aSyn aggregates in paragraph above.

Demasking

To disrupt the binding of aSyn specific auto-antibodies to aSyn likely present in patient sera and, therefore, preventing detection of these aSyn bound auto-antibodies by antigen-based methods (like ELISA or FACS), sera were pre-diluted in 10 mM Glycin pH2.6 at a dilution of 1:16.7 for 5 min. 5 μl of the acidified serum were then co-incubated with 3 μl of aSyn for another 5 min. Then the mixture was neutralized by addition of 92 μl of 0.5% BSA/PBS and incubated for 20 to 60 min. Washing steps and incubation with secondary antibody were performed as described above for non-demasked serum.

Results aSyn-Aggregates: Oligomerization and Fibril Formation

The formation of aSyn-aggregates from monomeric aSyn has been intensively investigated under multiple conditions in the recent years. It has been found that aggregation of aSyn peptides is very much dependent on different conditions including pH, temperature, buffer composition and protein concentration. Aggregation starts with the formation of β-hairpins from monomers leading to soluble oligomers. Conformational transition into parallel β-sheets then leads to the formation of fibrils and fibrillar aggregates, which can be precipitated by centrifugation.

According to the present invention, aSyn-aggregates (full length human aSyn 1-140) were generated. These aSyn-aggregates can be detected using FACS-analysis. As described in Material and Methods (MM), seedless soluble aSyn peptides were incubated for this purpose for 20 h at 37° C. at a concentration of 35 μM. As shown in FIG. 1A (upper panel) a clear homogenous population of aSyn aggregates could be detected by FACS analysis. The size distribution of aSyn-aggregates (defined by forward scatter FSC-A) was analyzed using calibrated size beads ranging from 1 to 15 μm (Flow Cytometry Size Calibration Kit (Cat.#F-13838) by Molecular probes) (FIG. 1 lower panel). Using this analysis it was shown that the size of generated aSyn-aggregates ranged as expected from sub-micrometer range up to 10 μm in which most of the generated aggregates range from ~500 nm up to 2 μm.

Reactivity of mAbs with aSyn-Aggregates

To define whether aSyn-aggregates allow the binding of aSyn-specific antibodies and to determine whether such an interaction can be monitored using the here described FACS-based assay another set of experiments was undertaken. For this purpose, aSyn-aggregates as well as Aβ1-42 aggregates (made according to the disclosure in the international application PCT/EP2012/068494) were generated and were incubated with monoclonal antibodies specific either for aSyn (LB509) or Aβ1-42 (3A5). Additionally both forms of aggregates where incubated with the unspecific control mAB D129. As shown in FACS histograms in FIG. 2, the monoclonal antibody LB509 binds exclusively aSyn aggregates whereas mAb 3A5 interacts only with Aβ1-42 aggregates. Furthermore, the irrelevant mAb D129 used as isotype control does neither react with aSyn nor with Aβ-aggregates. This shows that the described FACS-based assay allows the detection of aSyn antibodies in a highly specific manner.

Defining the Linear Range of Antibody Reactivity Against aSyn in FACS Assay and ELISA System To define the upper and lower limits of the linear analytic measurement range, titration experiments were performed using the mAb LB509 (FIG. 3).

Calculations to estimate the linear range in Excel using the Pearson's coefficient of determination resulted in R2-values >0.9966 for LB509 concentrations in the range of 80-0.128 ng/ml in the FACS aggregation assay, thereby going over three log stages. Determination of linearity in ELISA resulted in a linear range between 15.625 ng/ml and 0.489 ng/ml thereby going over only two log-stages. A $R^2$-value of 1 would indicate 100% linearity.

Defining the Sensitivity of FACS Aggregation Assay and ELISA for aSyn Binding of Specific Autoantibodies in Sera and CSF of Animals Treated with aSyn Specific Vaccines The aim of this experiment was to define and compare the detection limits of two independent detection methods (ELISA and the FACS-based assay) for aSyn-reactivity of sera and CSF samples derived from animals vaccinated with an aSyn specific vaccine. aSyn was therefore immobilized onto Maxisorp microtiter plates for ELISA measurements. Alternatively, aSyn aggregates were generated for FACS analysis. Subsequently, a dilution series of three different sera or a 1:100 dilution of 20 different murine CSF samples were applied to the individual systems and either OD at 405 nm values in case of ELISA or fluorescence intensity (MFI values) in case of FACS assay was defined. For comparison reasons signal to noise ratio was evaluated for different serum- (FIGS. 4A, B, C) and CSF- (FIG. 4D) measurements and signals were expressed as fold-background-signal (×BG).

Higher sensitivity of the FACS aggregation assay was confirmed by titration of sera from immunized mice. Sera from mouse 2 (B) and 3 (C) showed a MFI signal above 2×BG even at a dilution of 1:125,000 with 2×BG for mouse two and 3.11×BG for mouse 3 respectively, whereas no signal could be detected in ELISA with this serum dilution. Also the MFI signal measured with serum from mouse 1 (C) resulted in MFI of 4.45×BG at a dilution of 1:25,000 compared to no specific signal in ELISA with this dilution.

Furthermore, CSF samples from 20 mice were also analysed with both assays. Comparison of the two methods using a 1:100 dilution of the CSF samples resulted in only one out of 20 samples reaching a significant signal detection in ELISA (2.02×BG for mouse 8) whereas 17 out of 20 samples showed a MFI signal >2×BG when measured in the FACS aggregation assay. Analysing the CSF sample from mouse 2 resulted in an MFI signal of almost 30×BG. The same CSF sample did not deliver a positive signal in the ELISA measurement.

This shows that the newly developed FACS-based assay to detect aSyn-specific auto-antibodies is up to 30 times more sensitive than conventional assay systems such as ELISA.

Defining the aSyn Reactivity of Human Autoantibodies Using IVIG

IVIG (intravenous immunoglobulin) is a commercially available blood product. It contains the pooled IgG fraction extracted from plasma derived from healthy donors (human plasma from at least 1000 donors). It has been shown that IVIG preparations contain naturally occurring antibodies (autoantibodies) specific for aSyn-peptides.

The aim of this experiment was to define whether the here described technology offers the possibility to detect aSyn-specific autoantibodies in IVIG (IVIG-Subcuvia, purchased from Baxter, Austria) in an effective way.

For this purpose aSyn aggregates were generated for FACS analysis. Subsequently, different IVIG dilutions ranging from 200 μg-64 ng/ml) were applied to the aggregates and fluorescence intensity (MFI values) were defined. As depicted in FIG. 5, the FACS-based assay provided strong fluorescence signals showing that the newly developed FACS-based assay to detect aSyn-specific autoantibodies is highly sensitive for aSyn autoantibodies.

Reactivity of mAbs with Mixed-Aggregates

To define whether and to which extent mixed-aggregates allow the binding of aSyn, Aβ1-42, and p(E)Aβ3-42 specific antibodies and to determine whether such an interaction can be monitored using the here described FACS-based assay another set of experiments was undertaken. For this purpose, in addition to pure aSyn-aggregates, Aβ1-42 aggregates and p(E)Aβ3-42 also equimolar mixtures or aggregate-mixtures with different ratios of individual proteins were generated as described in MM. These aggregates were then incubated with monoclonal antibodies specific either for aSyn (LB509) or Aβ1-42 (3A5) and p(E)Aβ3-42 (D129) and the mAB-binding pattern of the mixed aggregates was determined.

The reactivity of these mAbs to three different aggregate substrates (established by mixing equimolar amounts of indicated peptides) is depicted in FIG. 6. As shown in FACS PE-histograms, the monoclonal antibody 3A5 binds exclusively mixtures which contain Aβ1-42 aggregates (6A+B) whereas it shows no reactivity to the p(E)Aβ3-42/aSyn aggregate mixture (6C). The anti-p(E)Aβ3-42mAB D129 binds only mixtures that contain p(E)Aβ3-42 (6E+F) but shows no reactivity to Aβ1-42/aSyn (6D). Furthermore, the aSyn specific mAB LB509 reacts only with aggregate mixtures containing aSyn (6G+I) but does not react with the Aβ1-42/p(E)Aβ3-42 aggregate mixture (6H). This shows first that mixed aggregates can be generated containing different peptides and second that these aggregates react specifically with the respective mAbs.

Formation of Mixed Aggregates with Differentially Labelled Peptides

As described in MM equimolar mixed aggregates with differentially fluorescent-labelled Aβ1-42 and α-Synuclein peptides were generated. Therefore, equimolar ratios of Aβ1-42-Hilyte-555 (detectable in the PE-channel) and aSyn-Hilyte-488 (detectable in the FITC-channel) were mixed and aggregates were generated by overnight incubation. After incubation the mixed aggregates were analysed using the FACS Canto II. Acquired aggregates with a size range of 0.5-10 μm were gated in P1 in the FSC-A/SSC-A and P1 was further evaluated in the PE/FITC-dot plot to determine the contribution of Aβ1-42-Hilyte-555 (PE) and aSyn-Hilyte-488 (FITC). Co-incubation of Aβ1-42-Hilyte-555 and aSyn-Hilyte-488 resulted in mixed aggregates which were ~90% double positive indicating a homogenous distribution of Aβ1-42 and aSyn within the aggregate population.

In a further experiment the reactivity of specific α-Aβ1-42- and aSyn-mAB against mixed aggregates with different peptide constitutions was examined and the p(E)Aβ3-42 specific AB was used as negative control. Therefore a quantitative, symmetric titration series using monomeric Aβ1-42 and aSyn was used to generate different mixed-aggregates-substrates before sample preparation. In detail 35 μM monomeric solutions of Aβ1-42 and aSyn were mixed in the ratios as shown in Table 1 and the PE-MFI was determined after sample preparation.

TABLE 1

|  |  | % | μl |
|---|---|---|---|
| Substrate 1: | Aβ1-42/aSyn | 100/0 | 100/0 |
| Substrate 2: | Aβ1-42/aSyn | 99.9/0.1 | 99.9/0.1 |
| Substrate 3: | Aβ1-42/aSyn | 99/1 | 99/1 |
| Substrate 4: | Aβ1-42/aSyn | 90/10 | 90/10 |
| Substrate 5: | Aβ1-42/aSyn | 50/50 | 50/50 |
| Substrate 6: | Aβ1-42/aSyn | 10/90 | 10/90 |
| Substrate 7: | Aβ1-42/aSyn | 1/99 | 1/99 |
| Substrate 8: | Aβ1-42/aSyn | 0.1/99.9 | 0.1/99.9 |
| Substrate 9: | Aβ1-42/aSyn | 0/100 | 0/100 |

As expected there was no reactivity of the unspecific control AB D129 and also no reactivity with the aSyn specific AB LB509 when 100% Aβ1-42 aggregates were used as a substrate. But the titration series revealed that as soon as 0.1%/1% of aSyn was mixed with 99.9/99% of Aβ1-42, it is sufficient to induce a strong reactivity of the aSyn specific AB LB509 which was even stronger than the signals reached when LB509 was incubated with 100% aSyn-aggregates. One reason for this could be that aSyn alone forms aggregates with very tightly packed epitopes which inhibits the mAB to access all available epitopes because of sterical hindrance. On the other hand, in the mixed aggregates aSyn is incorporated in way that all available epitopes can be accessed by the mAB without blocking itself and therefore the PE-MFI signal is increased compared to measurements when 100% aSyn aggregates are used as a substrate.

Defining aSyn Amyloid Antibodies in Human Blood Derived from PD Patients a. Reactivity of IgG to aSyn Serum samples derived from PD patients (n=30, ~60-80 years old) are analyzed for naturally occurring aSyn-specific antibody content using aSyn-aggregates and FACS analysis as described above. Naturally occurring antibodies specific for aSyn-aggregates are detected in all samples tested. Results show that naturally occurring antibodies specific for aSyn aggregates are detected in all samples tested although the level of auto-antibodies clearly differs from patient to patient (FIG. 10 A)

b. Reactivity of IgM to Different aSyn-Aggregates

In a next set of experiments aSyn-aggregate specific IgM reactivity is defined in the same set of serum samples as described above. Naturally occurring antibodies of IgM isotype specific for aSYn-aggregates are detected in all samples tested. Again comparable to reactivitiy of IgG antibodies, a different level of auto-antibodies could be detected within this set of PD-patients (FIG. 10 B).

The invention claimed is:

1. A method for detecting alpha synuclein (aSyn)-specific antibodies in a fluid biological sample comprising:
   contacting the fluid biological sample with aSyn-comprising-aggregates to allow aSyn-specific antibodies in the fluid biological sample to bind to the aSyn-comprising-aggregates, and
   detecting an amount of the aSyn-specific antibodies bound to the aSyn-comprising-aggregates by fluorescence activated cell sorting (FACS),
   wherein the aSyn-comprising-aggregates are adjusted to have a size of 50 nm to 15 µm.

2. The method according to claim 1, wherein the aSyn-specific antibodies are human antibodies.

3. The method according to claim 1, wherein the aSyn-specific antibodies are autoantibodies.

4. The method according to claim 1, wherein the aSyn-comprising-aggregates are adjusted to have a size of 100 nm to 10 µm.

5. The method according to claim 1, further comprising preparing the aSyn-comprising-aggregates, prior to contacting the biological sample, by incubating aSyn at a pH of 2 to 9 for at least 20 min.

6. The method according to claim 1, wherein the biological sample is contacted with 0.01 µM to 10 µM of the aSyn-comprising-aggregates.

7. The method according to claim 1, wherein the biological sample is human blood or a sample derived from human blood.

8. The method according to claim 1, wherein the biological sample is contacted with the aSyn-comprising-aggregates for at least 10 min.

9. The method according to claim 1, further comprising demasking the aSyn-specific antibodies in the biological sample before the contacting.

10. The method according to claim 1, wherein:
    the biological sample is a sample taken from a patient undergoing or supposed to undergo an aSyn immunotherapy, and
    the detected amount of aSyn-specific antibodies is correlated to a proteinopathy-related diagnosis result of the patient at the time the biological sample is taken.

11. The method according to claim 10, wherein the method is performed at least twice on the patient.

12. The method according to claim 11, wherein the method is performed at least once each six months.

13. The method according to claim 11, wherein the method is performed at least once each month.

14. A method for diagnosing proteinopathies, comprising:
    contacting a fluid biological sample with alpha synuclein (aSyn)-comprising-aggregates to allow aSyn-specific antibodies in the biological sample to bind to the aSyn-comprising-aggregates, and
    detecting an amount of the aSyn-specific antibodies bound to the aSyn-comprising-aggregates by fluorescence activated cell sorting (FACS),
    wherein the aSyn-comprising-aggregates are adjusted to have a size of 50 nm to 15 µm.

15. The method according to claim 1, wherein the aSyn-specific antibodies are human IgG antibodies.

16. The method according to claim 1, wherein the aSyn-comprising aggregates are adjusted to have a size of from 200 nm to 5 µm.

17. The method according to claim 1, wherein the aSyn-comprising-aggregates are prepared by incubating aSyn at a pH of 2 to 9 for at least 4 h.

18. The method according to claim 1, wherein the biological sample is human plasma; human cerebrospinal fluid or human lymph.

19. The method according to claim 1, wherein the biological sample is contacted with the aSyn-comprising-aggregates for 20 min to 2 h.

* * * * *